United States Patent
Chen et al.

(10) Patent No.: US 7,557,101 B2
(45) Date of Patent: Jul. 7, 2009

(54) 4,5,6,7-TETRAHYDRO-THIENO[3,2-C] PYRIDINE DERIVATIVES

(75) Inventors: Li Chen, Shanghai (CN); Wayne Wen Lai, Shanghai (CN); Matthias Nettekoven, Grenzach-Wyhlen (DE); Olivier Roche, Folgensbourg (FR); Deye Zheng, Shanghai (CN)

(73) Assignee: Hoffman-La Roche Inc., Nutley, NJ (US)

( * ) Notice: Subject to any disclaimer, the term of this patent is extended or adjusted under 35 U.S.C. 154(b) by 45 days.

(21) Appl. No.: 11/942,754

(22) Filed: Nov. 20, 2007

(65) Prior Publication Data
US 2008/0146558 A1      Jun. 19, 2008

(30) Foreign Application Priority Data
Dec. 8, 2006    (EP)   ................. 06125721

(51) Int. Cl.
*A61K 31/4365*   (2006.01)
*A61K 31/496*    (2006.01)
*A61K 31/5377*   (2006.01)
*C07D 495/04*    (2006.01)

(52) U.S. Cl. ............... 514/233.8; 514/253.04; 514/301; 544/127; 544/362; 546/114

(58) Field of Classification Search ........... None
See application file for complete search history.

(56) References Cited

U.S. PATENT DOCUMENTS

2007/0232591 A1*   10/2007   Gao et al. .............. 514/217.01

FOREIGN PATENT DOCUMENTS

EP    0 054 442 A1   6/1982
EP    0 421 861 A1   4/1991

OTHER PUBLICATIONS

Dvorak, C.A., 4- Phenoxypiperidines: Potent, Conformationally Restricted, Non-Imidazole Histamine $H_3$ Antagonists XP-002472995.
Stark, H., Recent Advances in Histamine $H_3/H_4$ receptor ligands, XP002298271.
Berlin, M., Recent Advances in the development of Histamine $H_3$, antagonists, XP002468038.

* cited by examiner

*Primary Examiner*—Emily Bernhardt
(74) *Attorney, Agent, or Firm*—George W. Johnston; Dennis P. Tramaloni; Samuel H. Megerditchian

(57) ABSTRACT

The present invention relates to compounds of formula I

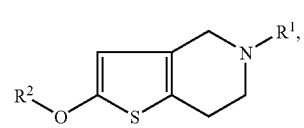

wherein $R^1$ and $R^2$ are as defined in the description and claims, and pharmaceutically acceptable salts thereof. The compounds are useful for the treatment and/or prevention of diseases which are associated with the modulation of H3 receptors.

25 Claims, No Drawings

4,5,6,7-TETRAHYDRO-THIENO[3,2-C] PYRIDINE DERIVATIVES

PRIORITY TO RELATED APPLICATION(S)

This application claims the benefit of European Patent Application No. 06125721.8, filed Dec. 8, 2006, which is hereby incorporated by reference in its entirety.

FIELD OF THE INVENTION

The present invention is concerned with new 4,5,6,7-tetrahydro-thieno[3,2-c]pyridine derivatives, their manufacture, pharmaceutical compositions containing them and their use as medicaments. The active compounds of the present invention are useful in treating obesity and other disorders.

In particular, the present invention relates to compounds of the general formula

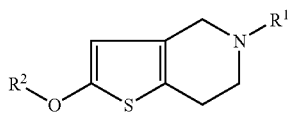

and pharmaceutically acceptable salts thereof.

The compounds of formula I are antagonists and/or inverse agonists at the histamine 3 receptor (H3 receptor).

All document cited or relied upon below are expressly incorporated herein by reference.

BACKGROUND OF THE INVENTION

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tuberomammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

SUMMARY OF THE INVENTION

In an embodiment of the present invention, provided is a compound of formula (I):

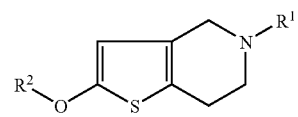

wherein:
$R^1$ is selected from the group consisting of
  —CO—$R^3$, wherein
    $R^3$ is selected from the group consisting of
    lower alkyl,
    lower cycloalkylalkyl, wherein the cycloalkyl ring may be unsubstituted or substituted with one or two groups independently selected from lower alkyl, and
    phenyl, wherein the phenyl ring may be unsubstituted or substituted with one or two groups independently selected from lower alkyl, cyano, halogen, lower halogenalkyl and lower alkoxy,
  —CO—$NR^4R^5$, wherein
    $R^4$ and $R^5$ independently from each other are selected from the group consisting of hydrogen, lower alkyl, lower alkoxyalkyl,
    phenyl unsubstituted or substituted with one or two groups independently selected from lower alkyl, halogen, lower alkoxy and lower halogenalkyl, and
    lower phenylalkyl, wherein phenyl is unsubstituted or substituted with one or two groups independently selected from lower alkyl, halogen, lower alkoxy and lower halogenalkyl, or R$^4$ and R$^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy, and —SO$_2$—R$^6$, wherein R$^6$ is selected from the group consisting of lower alkyl, lower alkoxyalkyl, lower cycloalkylalkyl, wherein the cycloalkyl ring may be unsubstituted or substituted with one or two groups independently selected from lower alkyl, halogen and lower alkoxy, and phenyl, wherein the phenyl ring may be unsubstituted or substituted with one or two groups independently selected from lower alkyl, cyano, halogen, lower halogenalkyl and lower alkoxy;

R$^2$ is a group selected from

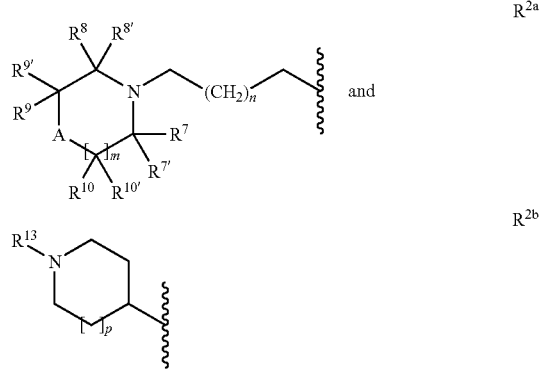

wherein m is 0, 1 or 2;

n is 0, 1 or 2;

A is selected from —CR$^{11}$R$^{11'}$—, O, S or —NR$^{12}$;

R$^7$, R$^{7'}$, R$^8$, R$^{8'}$, R$^9$, R$^{9'}$, R$^{10}$, R$^{10'}$, R$^{11}$ and R$^{11'}$ independently from each other are hydrogen or lower alkyl;

R$^{12}$ is hydrogen or lower alkyl;

p is 0, 1 or 2; and

R$^{13}$ is lower alkyl or cycloalkyl;

and pharmaceutically acceptable salts thereof.

In another embodiment of the present invention, provided is a pharmaceutical composition, comprising a therapeutically effective amount of a compound according to claim 1 as well as a pharmaceutically acceptable carrier and/or adjuvant.

DETAILED DESCRIPTION

The invention provides for selective, directly acting H3 receptor antagonists respectively inverse agonists. Such antagonists/inverse agonists are useful as therapeutically active substances, particularly in the treatment and/or prevention of diseases which are associated with the modulation of H3 receptors.

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "C$_1$-C$_7$-alkyl", alone or in combination, signifies a straight-chain or branched-chain alkyl group with 1 to 7 carbon atoms, preferably a straight or branched-chain alkyl group with 1 to 6 carbon atoms and particularly preferred a straight or branched-chain alkyl group with 1 to 4 carbon atoms Examples of straight-chain and branched C$_1$-C$_7$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl and ethyl and most preferred methyl.

The term "cycloalkyl" or "C$_{3-7}$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclopropyl, cyclopentyl and cyclohexyl.

The term "lower cycloalkylalkyl" or "C$_{3-7}$-cycloalkyl-C$_{1-7}$-alkyl" refers to lower alkyl groups as defined above wherein at least one of the hydrogen atoms of the lower alkyl group is replaced by cycloalkyl. A preferred example is cyclohexylmethyl.

The term "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec. butoxy and tert.-butoxy, preferably methoxy and ethoxy and most preferred methoxy.

The term "lower alkoxyalkyl" or "C$_{1-7}$-alkoxy-C$_{1-7}$-alkyl" refers to lower alkyl groups as defined above wherein at least one of the hydrogen atoms of the lower alkyl groups is replaced by an alkoxy group, preferably methoxy or ethoxy. Among the preferred lower alkoxyalkyl groups are 2-methoxyethyl or 3-methoxypropyl.

The term "halogen" refers to fluorine, chlorine, bromine and iodine, with fluorine, chlorine and bromine being preferred.

The term "lower halogenalkyl" or "halogen-C$_{1-7}$-alkyl" refers to lower alkyl groups as defined above wherein at least one of the hydrogen atoms of the lower alkyl group is replaced by a halogen atom, preferably fluoro or chloro, most preferably fluoro. Among the preferred halogenated lower alkyl groups are trifluoromethyl, difluoromethyl, fluoromethyl and chloromethyl, with trifluoromethyl being especially preferred.

The term "carbamoyl" refers to the group —CO—NH$_2$.

The term "lower phenylalkyl" or "phenyl-C$_{1-7}$-alkyl" to lower alkyl groups as defined above wherein at least one of the hydrogen atoms of the lower alkyl group is replaced by a phenyl group. Preferred lower phenylalkyl groups are benzyl or phenethyl.

The term "form a 4-, 5-, 6- or 7-membered heterocyclic ring optionally containing a further heteroatom selected from nitrogen, oxygen or sulfur" refers to a saturated N-heterocyclic ring, which may optionally contain a further nitrogen, oxygen or sulfur atom, such as azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, or azepanyl. A "4-, 5-, 6- or 7-membered heterocyclic ring containing a sulfinyl group or a sulfonyl group" means a N-heterocyclic ring that contains a —S(O)— group or a —SO$_2$— group, for example 1-oxothiomorpholinyl or 1,1-dioxothiomorpholinyl. The heterocyclic ring may be unsubstituted or substituted by one, two or three groups independently selected from lower alkyl, halogen, cyano, lower alkoxy and phenyl, wherein phenyl is unsubstituted or substituted with one or two groups independently selected from lower alkyl, halogen and lower alkoxy.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared form addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term pharmaceutically acceptable salts also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

In detail, the present invention relates to compounds of the general formula

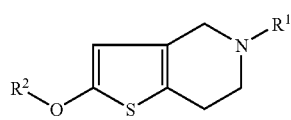

I wherein $R^1$ is selected from the group consisting of
—CO—$R^3$, wherein
$R^3$ is selected from the group consisting of
lower alkyl
lower cycloalkylalkyl, wherein the cycloalkyl ring may be unsubstituted or substituted with one or two groups independently selected from lower alkyl;
phenyl, wherein the phenyl ring may be unsubstituted or substituted with one or two groups independently selected from lower alkyl, cyano, halogen, lower halogenalkyl and lower alkoxy,
—CO—NR$^4$R$^5$, wherein
$R^4$ and $R^5$ independently from each other are selected from the group consisting of hydrogen, lower alkyl, lower alkoxyalkyl,
phenyl unsubstituted or substituted with one or two groups independently selected from lower alkyl, halogen, lower alkoxy and lower halogenalkyl, and lower phenylalkyl, wherein phenyl is unsubstituted or substituted with one or two groups independently selected from lower alkyl, halogen, lower alkoxy and lower halogenalkyl,
or $R^4$ and $R^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy, and
—SO$_2$—R$^6$, wherein
$R^6$ is selected from the group consisting of
lower alkyl, lower alkoxyalkyl,
lower cycloalkylalkyl, wherein the cycloalkyl ring may be unsubstituted or substituted with one or two groups independently selected from lower alkyl, halogen and lower alkoxy;
phenyl, wherein the phenyl ring may be unsubstituted or substituted with one or two groups independently selected from lower alkyl, cyano, halogen, lower halogenalkyl and lower alkoxy;

$R^2$ is a group selected from

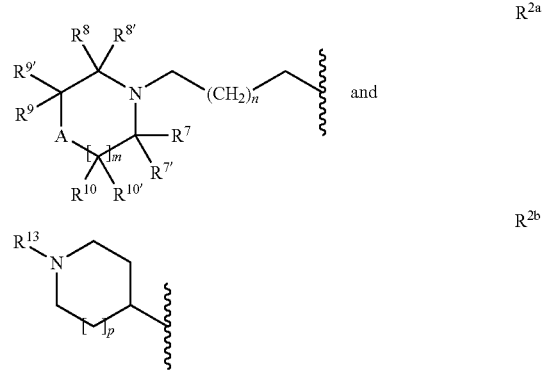

wherein
m is 0, 1 or 2;
n is 0, 1 or 2;
A is selected from —CR$^{11}$R$^{11'}$—, O, S or —NR$^{12}$;
$R^7$, $R^{7'}$, $R^8$, $R^{8'}$, $R^9$, $R^{9'}$, $R^{10}$, $R^{10'}$, $R^{11}$ and $R^{11'}$ independently from each other are hydrogen or lower alkyl;
$R^{12}$ is hydrogen or lower alkyl;
p is 0, 1 or 2; and
$R^{13}$ is lower alkyl or cycloalkyl;

and pharmaceutically acceptable salts thereof.

Preferred compounds of formula I of the present invention are compounds of formula I, wherein $R^1$ is —CO—$NR^4R^5$ and wherein $R^4$ and $R^5$ independently from each other are selected from the group consisting of hydrogen, lower alkyl, lower alkoxyalkyl, phenyl unsubstituted or substituted with one or two groups independently selected from lower alkyl, halogen, lower alkoxy and lower halogenalkyl, and lower phenylalkyl, wherein phenyl is unsubstituted or substituted with one or two groups independently selected from lower alkyl, halogen, lower alkoxy and lower halogenalkyl, or $R^4$ and $R^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy.

More preferred are compounds of formula I, wherein $R^1$ is —CO—$NR^4R^5$ and wherein $R^4$ and $R^5$ independently from each other are selected from the group consisting of hydrogen, lower alkyl, lower alkoxyalkyl, phenyl unsubstituted or substituted with one or two groups independently selected from lower alkyl, halogen, lower alkoxy and lower halogenalkyl, and lower phenylalkyl, wherein phenyl is unsubstituted or substituted with one or two groups independently selected from lower alkyl, halogen, lower alkoxy and lower halogenalkyl.

Also more preferred are those compounds of formula I according to the invention, wherein $R^1$ is —CO—$NR^4R^5$ and wherein $R^4$ and $R^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy.

Within this group, those compounds are preferred, wherein $R^1$ is —CO—$NR^4R^5$ and wherein $R^4$ and $R^5$ together with the nitrogen atom to which they are attached form a heterocyclic ring selected from the group consisting of pyrrolidinyl, piperidinyl, piperazinyl and morpholinyl, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy.

Furthermore, compounds of formula I according to the present invention are preferred, wherein $R^1$ is —CO—$R^3$ and wherein $R^3$ is selected from the group consisting of lower alkyl, lower cycloalkylalkyl, wherein the cycloalkyl ring may be unsubstituted or substituted with one or two groups independently selected from lower alkyl, and phenyl, wherein the phenyl ring may be unsubstituted or substituted with one or two groups independently selected from lower alkyl, cyano, halogen, lower halogenalkyl and lower alkoxy.

Compounds of formula I, wherein $R^1$ is —CO—$R^3$ and wherein $R^3$ is lower alkyl or lower cycloalkylalkyl, wherein the cycloalkyl ring may be unsubstituted or substituted with one or two groups independently selected from lower alkyl, are especially preferred, with those compounds, wherein $R^3$ is lower alkyl, being more preferred, and with those compounds of formula I, wherein $R^3$ is $C_{4-5}$-alkyl such as isobutyl, being most preferred.

Also preferred are compounds of formula I according to the invention, wherein $R^1$ is —CO—$R^3$ and wherein $R^3$ is phenyl, wherein the phenyl ring may be unsubstituted or substituted with one or two groups independently selected from lower alkyl, cyano, halogen, lower halogenalkyl and lower alkoxy.

Further preferred are compounds of formula I according to the present invention, wherein $R^1$ is $SO_2$—$R^6$ and wherein $R^6$ is selected from the group consisting of lower alkyl, lower alkoxyalkyl, lower cycloalkylalkyl, wherein the cycloalkyl ring may be unsubstituted or substituted with one or two groups independently selected from lower alkyl, halogen and lower alkoxy, and phenyl, wherein the phenyl ring may be unsubstituted or substituted with one or two groups independently selected from lower alkyl, cyano, halogen, lower halogenalkyl and lower alkoxy.

Within this group, compounds of formula I are preferred, wherein $R^1$ is $SO_2$—$R^6$ and wherein $R^6$ is lower alkyl or phenyl, wherein the phenyl ring may be unsubstituted or substituted with one or two lower alkyl groups.

Further preferred compounds of formula I according to the present invention are those compounds, wherein $R^2$ signifies

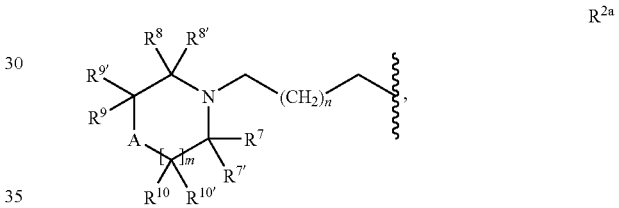

wherein m is 0 or 1;

n is 1;

A is selected from —$CR^{11}R^{11'}$—, O, S or —$NR^{12}$;

$R^7$, $R^{7'}$, $R^8$, $R^{8'}$, $R^9$, $R^{9'}$, $R^{10}$, $R^{10'}$, $R^{11}$ and $R^{11'}$ independently from each other are hydrogen or lower alkyl; and $R^{12}$ is hydrogen or lower alkyl.

Within this group, those compounds of formula I are preferred, wherein A is $CR^{11}R^{11'}$ and $R^7$, $R^{7'}$, $R^8$, $R^{8'}$, $R^9$, $R^{9'}$, $R^{10}$, $R^{10'}$, $R^{11}$ and $R^{11'}$ independently from each other are hydrogen or lower alkyl, with those compounds of formula I, wherein $R^7$, $R^{7'}$, $R^8$, $R^{8'}$, $R^9$, $R^{9'}$, $R^{10}$, $R^{10'}$, $R^{11}$ and $R^{11'}$ are hydrogen, being especially preferred.

Also preferred are compounds of formula I, wherein A is O, with those compounds of formula I, wherein A is O and $R^7$, $R^{7'}$, $R^8$, $R^{8'}$, $R^9$, $R^{9'}$, $R^{10}$ and $R^{10'}$ are hydrogen, being especially preferred.

Further preferred are compounds of formula I according to the invention, wherein $R^2$ signifies

wherein p is 0, 1 or 2; and $R^{13}$ is lower alkyl or cycloalkyl.

Within this group, those compounds are especially preferred, wherein $R^{13}$ is isopropyl or isobutyl.

Furthermore, compounds of formula I according to the invention are preferred, wherein p is 0 or 1.

Examples of Preferred Compounds of Formula I are the Following morpholin-4-yl-[2-(3-piperidin-1-yl-propoxy)-6,7-dihydro-4H-thieno[3,2-c]pyridin-5-yl]-methanone,
piperidin-1-yl-[2-(3-piperidin-1-yl-propoxy)-6,7-dihydro-4H-thieno[3,2-c]pyridin-5-yl]-methanone,
[2-(3-piperidin-1-yl-propoxy)-6,7-dihydro-4H-thieno[3,2-c]pyridin-5-yl]-pyrrolidin-1-yl-methanone,
(4-methyl-piperazin-1-yl)-[2-(3-piperidin-1-yl-propoxy)-6,7-dihydro-4H-thieno[3,2-c]pyridin-5-yl]-methanone,
(4-methoxy-piperidin-1-yl)-[2-(3-piperidin-1-yl-propoxy)-6,7-dihydro-4H-thieno[3,2-c]pyridin-5-yl]-methanone,
2-(3-piperidin-1-yl-propoxy)-6,7-dihydro-4H-thieno[3,2-c]pyridine-5-carboxylic acid diethylamide,
[2-(3-piperidin-1-yl-propoxy)-6,7-dihydro-4H-thieno[3,2-c]pyridin-5-yl]-(4-o-tolyl-piperazin-1-yl)-methanone,
2-(3-piperidin-1-yl-propoxy)-6,7-dihydro-4H-thieno[3,2-c]pyridine-5-carboxylic acid ethylamide,
2-(3-piperidin-1-yl-propoxy)-6,7-dihydro-4H-thieno[3,2-c]pyridine-5-carboxylic acid isopropylamide,
2-(3-piperidin-1-yl-propoxy)-6,7-dihydro-4H-thieno[3,2-c]pyridine-5-carboxylic acid isobutyl-amide,
2-(3-piperidin-1-yl-propoxy)-6,7-dihydro-4H-thieno[3,2-c]pyridine-5-carboxylic acid pentylamide,
2-(3-piperidin-1-yl-propoxy)-6,7-dihydro-4H-thieno[3,2-c]pyridine-5-carboxylic acid hexylamide,
2-(3-piperidin-1-yl-propoxy)-6,7-dihydro-4H-thieno[3,2-c]pyridine-5-carboxylic acid benzylamide,
2-(3-piperidin-1-yl-propoxy)-6,7-dihydro-4H-thieno[3,2-c]pyridine-5-carboxylic acid phenethyl-amide,
2-(3-piperidin-1-yl-propoxy)-6,7-dihydro-4H-thieno[3,2-c]pyridine-5-carboxylic acid (3-phenyl-propyl)-amide,
(4-phenyl-piperidin-1-yl)-[2-(3-piperidin-1-yl-propoxy)-6,7-dihydro-4H-thieno[3,2-c]pyridin-5-yl]-methanone,
[4-(2-methoxy-phenyl)-piperazin-1-yl]-[2-(3-piperidin-1-yl-propoxy)-6,7-dihydro-4H-thieno[3,2-c]pyridin-5-yl]-methanone,
2-(3-piperidin-1-yl-propoxy)-6,7-dihydro-4H-thieno[3,2-c]pyridine-5-carboxylic acid (2-methoxy-ethyl)-amide,
[4-(3,4-dimethyl-phenyl)-piperazin-1-yl]-[2-(3-piperidin-1-yl-propoxy)-6,7-dihydro-4H-thieno[3,2-c]pyridin-5-yl]-methanone,
(4-phenyl-piperazin-1-yl)-[2-(3-piperidin-1-yl-propoxy)-6,7-dihydro-4H-thieno[3,2-c]pyridin-5-yl]-methanone,
[4-(4-fluoro-phenyl)-piperazin-1-yl]-[2-(3-piperidin-1-yl-propoxy)-6,7-dihydro-4H-thieno[3,2-c]pyridin-5-yl]-methanone,
[4-(4-chloro-phenyl)-piperazin-1-yl]-[2-(3-piperidin-1-yl-propoxy)-6,7-dihydro-4H-thieno[3,2-c]pyridin-5-yl]-methanone,
5-benzenesulfonyl-2-(3-piperidin-1-yl-propoxy)-4,5,6,7-tetrahydro-thieno[3,2-c]pyridine,
2-(3-piperidin-1-yl-propoxy)-5-(toluene-4-sulfonyl)-4,5,6,7-tetrahydro-thieno[3,2-c]pyridine,
2-(3-piperidin-1-yl-propoxy)-5-(toluene-2-sulfonyl)-4,5,6,7-tetrahydro-thieno[3,2-c]pyridine,
5-ethanesulfonyl-2-(3-piperidin-1-yl-propoxy)-4,5,6,7-tetrahydro-thieno[3,2-c]pyridine,
2-(3-piperidin-1-yl-propoxy)-5-(propane-2-sulfonyl)-4,5,6,7-tetrahydro-thieno[3,2-c]pyridine,
5-(butane-1-sulfonyl)-2-(3-piperidin-1-yl-propoxy)-4,5,6,7-tetrahydro-thieno[3,2-c]pyridine,
5-methanesulfonyl-2-(3-piperidin-1-yl-propoxy)-4,5,6,7-tetrahydro-thieno[3,2-c]pyridine,
2-(4-methyl-cyclohexyl)-1-[2-(3-piperidin-1-yl-propoxy)-6,7-dihydro-4H-thieno[3,2-c]pyridin-5-yl]-ethanone,
(2,3-difluoro-phenyl)-[2-(3-piperidin-1-yl-propoxy)-6,7-dihydro-4H-thieno[3,2-c]pyridin-5-yl]-methanone,
3-methyl-1-[2-(3-piperidin-1-yl-propoxy)-6,7-dihydro-4H-thieno[3,2-c]pyridin-5-yl]-butan-1-one,
1-[2-(3-piperidin-1-yl-propoxy)-6,7-dihydro-4H-thieno[3,2-c]pyridin-5-yl]-butan-1-one,
(2-chloro-phenyl)-[2-(3-piperidin-1-yl-propoxy)-6,7-dihydro-4H-thieno[3,2-c]pyridin-5-yl]-methanone,
(3-chloro-phenyl)-[2-(3-piperidin-1-yl-propoxy)-6,7-dihydro-4H-thieno[3,2-c]pyridin-5-yl]-methanone,
2-ethyl-1-[2-(3-piperidin-1-yl-propoxy)-6,7-dihydro-4H-thieno[3,2-c]pyridin-5-yl]-butan-1-one,
morpholin-4-yl-[2-(3-pyrrolidin-1-yl-propoxy)-6,7-dihydro-4H-thieno[3,2-c]pyridin-5-yl]-methanone,
piperidin-1-yl-[2-(3-pyrrolidin-1-yl-propoxy)-6,7-dihydro-4H-thieno[3,2-c]pyridin-5-yl]-methanone,
pyrrolidin-1-yl-[2-(3-pyrrolidin-1-yl-propoxy)-6,7-dihydro-4H-thieno[3,2-c]pyridin-5-yl]-methanone,
(4-methoxy-piperidin-1-yl)-[2-(3-pyrrolidin-1-yl-propoxy)-6,7-dihydro-4H-thieno[3,2-c]pyridin-5-yl]-methanone,
(4-methyl-piperazin-1-yl)-[2-(3-pyrrolidin-1-yl-propoxy)-6,7-dihydro-4H-thieno[3,2-c]pyridin-5-yl]-methanone,
2-(3-pyrrolidin-1-yl-propoxy)-6,7-dihydro-4H-thieno[3,2-c]pyridine-5-carboxylic acid ethylamide,
2-(3-pyrrolidin-1-yl-propoxy)-6,7-dihydro-4H-thieno[3,2-c]pyridine-5-carboxylic acid isopropylamide,
2-(3-pyrrolidin-1-yl-propoxy)-6,7-dihydro-4H-thieno[3,2-c]pyridine-5-carboxylic acid isobutyl-amide,
2-(3-pyrrolidin-1-yl-propoxy)-6,7-dihydro-4H-thieno[3,2-c]pyridine-5-carboxylic acid pentylamide,
2-(3-pyrrolidin-1-yl-propoxy)-6,7-dihydro-4H-thieno[3,2-c]pyridine-5-carboxylic acid hexylamide,
2-(3-pyrrolidin-1-yl-propoxy)-6,7-dihydro-4H-thieno[3,2-c]pyridine-5-carboxylic acid (3-methoxy-propyl)-amide,
2-(3-pyrrolidin-1-yl-propoxy)-6,7-dihydro-4H-thieno[3,2-c]pyridine-5-carboxylic acid benzylamide,
2-(3-pyrrolidin-1-yl-propoxy)-6,7-dihydro-4H-thieno[3,2-c]pyridine-5-carboxylic acid phenethyl-amide,
2-ethyl-1-[2-(3-pyrrolidin-1-yl-propoxy)-6,7-dihydro-4H-thieno[3,2-c]pyridin-5-yl]-butan-1-one,
3-methyl-1-[2-(3-pyrrolidin-1-yl-propoxy)-6,7-dihydro-4H-thieno[3,2-c]pyridin-5-yl]-butan-1-one,
5-methanesulfonyl-2-(3-pyrrolidin-1-yl-propoxy)-4,5,6,7-tetrahydro-thieno[3,2-c]pyridine,
5-(butane-1-sulfonyl)-2-(3-pyrrolidin-1-yl-propoxy)-4,5,6,7-tetrahydro-thieno[3,2-c]pyridine,
5-benzenesulfonyl-2-(3-pyrrolidin-1-yl-propoxy)-4,5,6,7-tetrahydro-thieno[3,2-c]pyridine,
2-(3-pyrrolidin-1-yl-propoxy)-5-(toluene-4-sulfonyl)-4,5,6,7-tetrahydro-thieno[3,2-c]pyridine,
2-(3-pyrrolidin-1-yl-propoxy)-5-(toluene-2-sulfonyl)-4,5,6,7-tetrahydro-thieno[3,2-c]pyridine,
2-(3-pyrrolidin-1-yl-propoxy)-5-(toluene-3-sulfonyl)-4,5,6,7-tetrahydro-thieno[3,2-c]pyridine,
5-(4-ethyl-benzenesulfonyl)-2-(3-pyrrolidin-1-yl-propoxy)-4,5,6,7-tetrahydro-thieno[3,2-c]pyridine,
2-(3-pyrrolidin-1-yl-propoxy)-6,7-dihydro-4H-thieno[3,2-c]pyridine-5-carboxylic acid (3-phenyl-propyl)-amide,
(4-phenyl-piperidin-1-yl)-[2-(3-pyrrolidin-1-yl-propoxy)-6,7-dihydro-4H-thieno[3,2-c]pyridin-5-yl]-methanone,

[4-(2-methoxy-phenyl)-piperazin-1-yl]-[2-(3-pyrrolidin-1-yl-propoxy)-6,7-dihydro-4H-thieno[3,2-c]pyridin-5-yl]-methanone,
(4-phenyl-piperazin-1-yl)-[2-(3-pyrrolidin-1-yl-propoxy)-6,7-dihydro-4H-thieno[3,2-c]pyridin-5-yl]-methanone,
2-(3-pyrrolidin-1-yl-propoxy)-6,7-dihydro-4H-thieno[3,2-c]pyridine-5-carboxylic acid (2-methoxy-ethyl)-amide,
5-benzenesulfonyl-2-(1-isobutyl-piperidin-4-yloxy)-4,5,6,7-tetrahydro-thieno[3,2-c]pyridine,
2-(1-isobutyl-piperidin-4-yloxy)-5-(toluene-4-sulfonyl)-4,5,6,7-tetrahydro-thieno[3,2-c]pyridine,
2-(1-isobutyl-piperidin-4-yloxy)-5-(toluene-2-sulfonyl)-4,5,6,7-tetrahydro-thieno[3,2-c]pyridine,
2-(1-isobutyl-piperidin-4-yloxy)-5-(toluene-3-sulfonyl)-4,5,6,7-tetrahydro-thieno[3,2-c]pyridine,
(2-chloro-phenyl)-[2-(1-isobutyl-piperidin-4-yloxy)-6,7-dihydro-4H-thieno[3,2-c]pyridin-5-yl]-methanone,
(3-chloro-phenyl)-[2-(1-isobutyl-piperidin-4-yloxy)-6,7-dihydro-4H-thieno[3,2-c]pyridin-5-yl]-methanone,
2-(1-isobutyl-piperidin-4-yloxy)-5-methanesulfonyl-4,5,6,7-tetrahydro-thieno[3,2-c]pyridine,
5-ethanesulfonyl-2-(1-isobutyl-piperidin-4-yloxy)-4,5,6,7-tetrahydro-thieno[3,2-c]pyridine,
(2,3-difluoro-phenyl)-[2-(1-isobutyl-piperidin-4-yloxy)-6,7-dihydro-4H-thieno[3,2-c]pyridin-5-yl]-methanone,
[2-(1-isopropyl-piperidin-4-yloxy)-6,7-dihydro-4H-thieno[3,2-c]pyridin-5-yl]-morpholin-4-yl-methanone,
[2-(1-isopropyl-piperidin-4-yloxy)-6,7-dihydro-4H-thieno[3,2-c]pyridin-5-yl]-(4-methoxy-piperidin-1-yl)-methanone,
2-(1-isopropyl-piperidin-4-yloxy)-6,7-dihydro-4H-thieno[3,2-c]pyridine-5-carboxylic acid isopropylamide,
1-[2-(1-isopropyl-piperidin-4-yloxy)-6,7-dihydro-4H-thieno[3,2-c]pyridin-5-yl]-butan-1-one,
1-[2-(1-isopropyl-piperidin-4-yloxy)-6,7-dihydro-4H-thieno[3,2-c]pyridin-5-yl]-pentan-1-one,
1-[2-(1-isopropyl-piperidin-4-yloxy)-6,7-dihydro-4H-thieno[3,2-c]pyridin-5-yl]-2-(4-methyl-cyclohexyl)-ethanone,
(2-chloro-phenyl)-[2-(1-isopropyl-piperidin-4-yloxy)-6,7-dihydro-4H-thieno[3,2-c]pyridin-5-yl]-methanone,
2-(1-isopropyl-piperidin-4-yloxy)-5-methane-sulfonyl-4,5,6,7-tetrahydro-thieno[3,2-c]pyridine,
5-(butane-1-sulfonyl)-2-(1-isopropyl-piperidin-4-yloxy)-4,5,6,7-tetrahydro-thieno[3,2-c]pyridine,
5-benzenesulfonyl-2-(1-isopropyl-piperidin-4-yloxy)-4,5,6,7-tetrahydro-thieno[3,2-c]pyridine,
2-(1-isopropyl-piperidin-4-yloxy)-5-(toluene-2-sulfonyl)-4,5,6,7-tetrahydro-thieno[3,2-c]pyridine,
2-(1-isopropyl-piperidin-4-yloxy)-5-(toluene-3-sulfonyl)-4,5,6,7-tetrahydro-thieno[3,2-c]pyridine,
2-(1-isopropyl-piperidin-4-yloxy)-5-(toluene-4-sulfonyl)-4,5,6,7-tetrahydro-thieno[3,2-c]pyridine,
5-(4-ethyl-benzenesulfonyl)-2-(1-isopropyl-piperidin-4-yloxy)-4,5,6,7-tetrahydro-thieno[3,2-c]pyridine,
2-(1-isopropyl-pyrrolidin-3-yloxy)-6,7-dihydro-4H-thieno[3,2-c]pyridine-5-carboxylic acid isopropylamide,
[2-(1-isopropyl-pyrrolidin-3-yloxy)-6,7-dihydro-4H-thieno[3,2-c]pyridin-5-yl]-morpholin-4-yl-methanone,
2-ethyl-1-[2-(1-isopropyl-pyrrolidin-3-yloxy)-6,7-dihydro-4H-thieno[3,2-c]pyridin-5-yl]-butan-1-one,
1-[2-(1-isopropyl-pyrrolidin-3-yloxy)-6,7-dihydro-4H-thieno[3,2-c]pyridin-5-yl]-2-(4-methyl-cyclohexyl)-ethanone,
(2-chloro-phenyl)-[2-(1-isopropyl-pyrrolidin-3-yloxy)-6,7-dihydro-4H-thieno[3,2-c]pyridin-5-yl]-methanone,
(3-chloro-phenyl)-[2-(1-isopropyl-pyrrolidin-3-yloxy)-6,7-dihydro-4H-thieno[3,2-c]pyridin-5-yl]-methanone,
(2,3-difluoro-phenyl)-[2-(1-isopropyl-pyrrolidin-3-yloxy)-6,7-dihydro-4H-thieno[3,2-c]pyridin-5-yl]-methanone,
[2-(1-isopropyl-pyrrolidin-3-yloxy)-6,7-dihydro-4H-thieno[3,2-c]pyridin-5-yl]-pyrrolidin-1-yl-methanone,
1-[2-(1-isopropyl-pyrrolidin-3-yloxy)-6,7-dihydro-4H-thieno[3,2-c]pyridin-5-yl]-3-methyl-butan-1-one,
2-(1-isopropyl-pyrrolidin-3-yloxy)-5-methane-sulfonyl-4,5,6,7-tetrahydro-thieno[3,2-c]pyridine,
5-benzenesulfonyl-2-(1-isopropyl-pyrrolidin-3-yloxy)-4,5,6,7-tetrahydro-thieno[3,2-c]pyridine,
2-(1-isopropyl-pyrrolidin-3-yloxy)-5-(toluene-3-sulfonyl)-4,5,6,7-tetrahydro-thieno[3,2-c]pyridine,
5-(4-ethyl-benzenesulfonyl)-2-(1-isopropyl-pyrrolidin-3-yloxy)-4,5,6,7-tetrahydro-thieno[3,2-c]pyridine,
2-(1-isopropyl-pyrrolidin-3-yloxy)-5-(propane-2-sulfonyl)-4,5,6,7-tetrahydro-thieno[3,2-c]pyridine,
[2-(3-morpholin-4-yl-propoxy)-6,7-dihydro-4H-thieno[3,2-c]pyridin-5-yl]-phenyl-methanone,
2-(3-morpholin-4-yl-propoxy)-5-(toluene-2-sulfonyl)-4,5,6,7-tetrahydro-thieno[3,2-c]pyridine,
2-(3-morpholin-4-yl-propoxy)-6,7-dihydro-4H-thieno[3,2-c]pyridine-5-carboxylic acid (3-phenyl-propyl)-amide,
[2-(3-morpholin-4-yl-propoxy)-6,7-dihydro-4H-thieno[3,2-c]pyridin-5-yl]-(4-phenyl-piperidin-1-yl)-methanone,
[4-(4-methoxy-phenyl)-piperazin-1-yl]-[2-(3-morpholin-4-yl-propoxy)-6,7-dihydro-4H-thieno[3,2-c]pyridin-5-yl]-methanone, and pharmaceutically acceptable salts thereof.
Particularly preferred compounds of formula I of the present invention are the following:
morpholin-4-yl-[2-(3-piperidin-1-yl-propoxy)-6,7-dihydro-4H-thieno[3,2-c]pyridin-5-yl]-methanone,
[2-(3-piperidin-1-yl-propoxy)-6,7-dihydro-4H-thieno[3,2-c]pyridin-5-yl]-pyrrolidin-1-yl-methanone,
morpholin-4-yl-[2-(3-pyrrolidin-1-yl-propoxy)-6,7-dihydro-4H-thieno[3,2-c]pyridin-5-yl]-methanone,
(4-methyl-piperazin-1-yl)-[2-(3-pyrrolidin-1-yl-propoxy)-6,7-dihydro-4H-thieno[3,2-c]pyridin-5-yl]-methanone,
2-(3-pyrrolidin-1-yl-propoxy)-6,7-dihydro-4H-thieno[3,2-c]pyridine-5-carboxylic acid benzylamide,
2-ethyl-1-[2-(3-pyrrolidin-1-yl-propoxy)-6,7-dihydro-4H-thieno[3,2-c]pyridin-5-yl]-butan-1-one,
3-methyl-1-[2-(3-pyrrolidin-1-yl-propoxy)-6,7-dihydro-4H-thieno[3,2-c]pyridin-5-yl]-butan-1-one,
2-(3-pyrrolidin-1-yl-propoxy)-5-(toluene-2-sulfonyl)-4,5,6,7-tetrahydro-thieno[3,2-c]pyridine,
(4-phenyl-piperazin-1-yl)-[2-(3-pyrrolidin-1-yl-propoxy)-6,7-dihydro-4H-thieno[3,2-c]pyridin-5-yl]-methanone,
[2-(1-isopropyl-piperidin-4-yloxy)-6,7-dihydro-4H-thieno[3,2-c]pyridin-5-yl]-morpholin-4-yl-methanone,
[2-(1-isopropyl-piperidin-4-yloxy)-6,7-dihydro-4H-thieno[3,2-c]pyridin-5-yl]-(4-methoxy-piperidin-1-yl)-methanone,
2-(1-isopropyl-piperidin-4-yloxy)-6,7-dihydro-4H-thieno[3,2-c]pyridine-5-carboxylic acid isopropylamide,
1-[2-(1-isopropyl-piperidin-4-yloxy)-6,7-dihydro-4H-thieno[3,2-c]pyridin-5-yl]-pentan-1-one,
(2-chloro-phenyl)-[2-(1-isopropyl-piperidin-4-yloxy)-6,7-dihydro-4H-thieno[3,2-c]pyridin-5-yl]-methanone,
2-(1-isopropyl-piperidin-4-yloxy)-5-(toluene-2-sulfonyl)-4,5,6,7-tetrahydro-thieno[3,2-c]pyridine,
1-[2-(1-isopropyl-pyrrolidin-3-yloxy)-6,7-dihydro-4H-thieno[3,2-c]pyridin-5-yl]-2-(4-methyl-cyclohexyl)-ethanone, and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises coupling an amine of the formula II

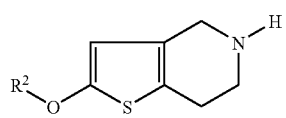

II wherein $R^2$ is as defined hereinbefore, with an halogenide of the formula III $R^1$—X    III wherein $R^1$ is as defined hereinbefore and X is halogen, in the presence of a base to obtain a compound of the formula I

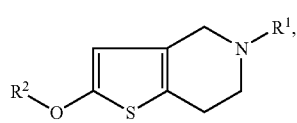

I and if desired, converting the compound obtained into a pharmaceutically acceptable salt.

The compounds of formula $R^1$—X (III) are acid halogenides, carbamoyl halogenides or sulfonyl halogenides wherein X signifies halogen such as e.g. chloride, iodide or bromide, preferably chloride. The base to be used is preferably a tertiary amine, with triethylamine (TEA) and diisopropylamine (DIPEA) being especially preferred.

The preparation of compounds of formula I of the present invention may be carried out in sequential or convergent synthetic routes. Syntheses of the compounds of the invention are shown in the following scheme. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

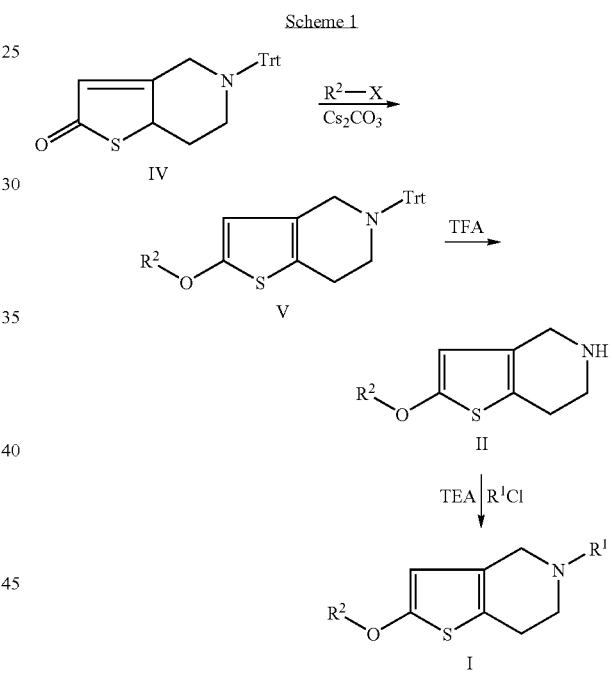

Scheme 1 a) 5-Trityl-5,6,7,7a-tetrahydro-4H-thieno[3,2-c]pyridin-2-one IV is described in literature (FR2576901A1) and can serve as a potential starting material for the synthesis of compounds of formula I.

Nucleophilic substitutions of aminoalkyl halides are widely described in literature (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999). However, it is convenient to transform aminoalkyl halides like $R^2$—X wherein $R^2$ is as defined herein before, with 5-trityl-5,6,7,7a-tetrahydro-4H-thieno[3,2-c]pyridin-2-one IV to the respective thieno[3,2-c]pyridine derivatives V in the presence of a base and a solvent. There is no particular restriction on the nature of the solvent to be employed, provided that it has no adverse effect on the reaction or the reagents involved and that it can dissolve the reagents, at least to some extent. Examples for suitable solvents include dimethylformamide (DMF), tetrahydrofuran (THF) and the like. There is no particular restriction on the nature of the base used in this stage, and any base commonly used in this type of reaction may equally be employed here. Examples of such bases include $Cs_2CO_3$, and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds of formula V.

b) Protecting group manipulations are widely described in literature. For reaction conditions described in literature affecting such reactions see for example: Handbook of Reagents for Organic Synthesis: Activating and Agents and Protecting Groups, Anthony J. Pearson, William R. Roush, Editors. John Wiley, Chichester, UK, 1999 or Protecting Groups, Philip J. Kocienski, Georg Thieme 1994, Stuttgart, N.Y. The trityl protected nitrogen in compounds of formula V can be liberated in many ways and under varying reaction conditions. However, it is convenient to cleave the protecting group from V under acidic conditions in the presence or the absence of a solvent to access thieno[3,2-c]pyridine derivatives II. There is no particular restriction on the nature of the solvent to be employed, provided that it has no adverse effect on the reaction or the reagents involved and that it can dissolve the reagents, at least to some extent. Even the acid itself can serve as the solvent. There is no particular restriction on the nature of the acid used in this stage, and any acid commonly used in this type of reaction may equally be employed here. Examples of such acids include trifluoroacetic acid (TFA), and the like. The reaction can take place over a wide range of temperatures, and the precise reaction temperature is not critical to the invention. It is convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds II.

c) The coupling of the amine functionality with electrophiles is widely described in literature and the procedures are known to those in the art (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999). The respective amines II can conveniently be transformed to the respective sulfonamides, amides or ureas through coupling of II with sulfonyl halogenides, acid halogenides, carbamoyl halogenides (preferably chlorides) or isocyanates (either commercially available or accessible by methods described in references or by methods known in the art; as appropriate). It is convenient to carry out the reaction in a solvent and in the presence of a base. There is no particular restriction on the nature of the solvent to be employed, provided that it has no adverse effect on the reaction or the reagents involved and that it can dissolve the reagents, at least to some extent. Examples for suitable solvents include dichloromethane (DCM), dioxane, tetrahydrofurane (THF), and the like. There is no particular restriction on the nature of the base used in this stage, and any base commonly used in this type of reaction may equally be employed here. Examples of such bases include triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield thieno[3,2-c]pyridine derivatives of formula I.

As described above, the compounds of formula I of the present invention can be used as medicaments for the treatment and/or prevention of diseases which are associated with the modulation of H3 receptors.

In this context, the expression diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastrointestinal disorders.

In a preferable aspect, the expression diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of medicaments for the treatment and/or prevention of diseases which are associated with the modulation of H3 receptors. The use of compounds of formula I as defined above for the preparation of medicaments for the treatment and/or prevention of obesity is preferred.

Furthermore, the present invention relates to the use of a compound of formula I for the manufacture of a medicament for the treatment and prevention of obesity in a patient who is also receiving treatment with a lipase inhibitor and particularly, wherein the lipase inhibitor is orlistat.

It is a further preferred embodiment of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a medicament for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an embodiment of the present invention.

The use of a compound of formula I in the manufacture of a medicament for the treatment and prevention of obesity in a patient who is also receiving treatment with a lipase inhibitor, preferably with tetrahydrolipstatin, is also an embodiment of the present invention.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an embodiment of the invention is the method as described above for the simultaneous, separate or sequential administration of a compound according to formula I and a lipase inhibitor, particularly tetrahydrolipstatin.

It is a further preferred embodiment to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an embodiment of the invention is the method as described above for the simultaneous, separate or sequential administration of a compound according to formula I and a therapeutically effective amount of an anti-diabetic agent.

The use of a compound of formula I in the manufacture of a medicament for the treatment and prevention of Type II diabetes in a patient who is also receiving treatment with an anti-diabetic agent is also an embodiment of the present invention.

It is a further preferred embodiment to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6)

lipoprotein synthesis inhibitors such as niacin, and the like; and 7) niacin receptor agonists such as nicotinic acid, and the like.

Also an embodiment of the invention is the method as described above for the simultaneous, separate or sequential administration of a compound according to formula I and a therapeutically effective amount of a lipid lowering agent.

The use of a compound of formula I in the manufacture of a medicament for the treatment and prevention of dyslipidemias in a patient who is also receiving treatment with a lipid lowering agent, is also an embodiment of the present invention.

It is a further preferred embodiment to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan (RO0610612), A308165, and the like. Also an embodiment of the invention is the method as described above for the simultaneous, separate or sequential administration of a compound according to formula I and a therapeutically effective amount of an anti-hypertensive agent.

The use of a compound of formula I in the manufacture of a medicament for the treatment and prevention of hypertension in a patient who is also receiving treatment with an anti-hypertensive agent, is also an embodiment of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula (I).

Binding Assay with $^3$H—(R)α-methylhistamine

Saturation binding experiments were performed using HR3-(CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard topcounter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human H3R—CHO cell line. An appropriate amount of protein, e.g. approximately 500 cpm binding of RAMH at Kd, were incubated for 1 hour at room temperature in 250 µl final volume in 96-well plates in presence of $^3$H(R)α-methylhistamine (1 nM final concentration=Kd). Non-specific binding was determined using a 200 fold excess of cold (R)α-methylhistamine dihydrobromide.

All compounds were tested at a single concentration in duplicate. Compounds that showed an inhibition of [$^3$H]-RAMH by more than 50% were tested again to determine $IC_{50}$ in a serial dilution experiment, meaning concentrations were spanning 10 points starting from $4.6 \times 10^{-6}$ M to $1.0 \times 10^{-9}$ M. The dilution factor was 1/2.15 for the whole series. The concentration at which 50% inhibition of the radioligand $^3$H(R)α-methylhistamine is obtained (the $IC_{50}$) is determined from the linear regression of a plot of the logarithm of the concentration versus percent inhibition measured for the different concentrations. Ki's were calculated from $IC_{50}$ based on Cheng-Prusoff equation (Cheng, Y, Prusoff, W H (1973) Biochem Pharmacol 22, 3099-3108): Ki=IC50/[1+D/Kd] wherein D is the concentration of the radioligand and Kd is the binding constant for the radioligand binding to the receptor under the conditions used in the competition experiment.

The compounds of the present invention exhibit $K_i$ values within the range of about 1 nM to about 1000 nM, preferably of about 1 nM to about 100 nM, and more preferably of about 1 nM to about 50 nM. The following table shows measured values for some selected compounds of the present invention.

|  | $K_i$ (nM) |
| --- | --- |
| Example 1 | 35.7 |
| Example 33 | 44.4 |
| Example 48 | 31.7 |
| Example 56 | 27.3 |
| Example 90 | 21.7 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner.

EXAMPLES

Intermediates

Intermediate 1

2-(3-Piperidin-1-yl-propoxy)-4,5,6,7-tetrahydro-thieno[3,2-c]pyridine a) Step 1: 2-(3-Piperidin-1-yl-propoxy)-5-trityl-4,5,6,7-tetrahydro-thieno[3,2-c]pyridine A mixture of 30 g (0.0755 mol) 5-trityl-5,6,7,7a-tetrahydro-4H-thieno[3,2-c]pyridin-2-one (FR2576901A1), 16.5 g (0.102 mol) 1-(3-chloropropyl)-piperidine (commercially available) and 61.5 g (0.1887 mol) $Cs_2CO_3$ in 1500 mL of DMF (dimethylformamide) solvent were heated to 80° C. for 10 h. After removal of the solvent, the residue was purified with column chromatograph to give 14 g of pure product as brown oil. (35.5% yield).

b) Step 2: 2-(3-Piperidin-1-yl-propoxy)-4,5,6,7-tetrahydro-thieno[3,2-c]pyridine A mixture of 14 g (0.268 mmol) 2-(3-piperidin-1-yl-propoxy)-5-trityl-4,5,6,7-tetrahydro-thieno[3,2-c]pyridine and 100 mL (1.30 mol) TFA (trifluoroacetic acid) in 200 mL of DCM (dichloromethane) was stirred at room temperature for 1 h. After evaporation under vacuo, the residue was dissolved in water, adjusted to basic pH with aqueous NH$_3$.H$_2$O and extracted with DCM. The organic phase was dried and concentrated to give 3.9 g of the product as brown oil. (73.6% yield)

Intermediate 2

2-(3-Pyrrolidin-1-yl-propoxy)-4,5,6,7-tetrahydro-thieno[3,2-c]pyridine

In analogy to the procedure described for the synthesis of 2-(3-piperidin-1-yl-propoxy)-4,5,6,7-tetrahydro-thieno[3,2-c]pyridine (intermediate 1) the title compound was prepared from 5-trityl-5,6,7,7a-tetrahydro-4H-thieno[3,2-c]pyridin-2-one (FR 2576901 A1) and 1-(3-chloro-propyl)-pyrrolidine (commercially available). The trityl-group was subsequently cleaved with TFA.

Intermediate 3

2-(1-Isobutyl-piperidin-4-yloxy)-4,5,6,7-tetrahydro-thieno[3,2-c]pyridine

In analogy to the procedure described for the synthesis of 2-(3-piperidin-1-yl-propoxy)-4,5,6,7-tetrahydro-thieno[3,2-c]pyridine (intermediate 1) the title compound was prepared from 5-trityl-5,6,7,7a-tetrahydro-4H-thieno[3,2-c]pyridin-2-one (FR 2576901 A1) and 4-bromo-1-isobutyl-piperidine (commercially available). The trityl-group was subsequently cleaved with TFA.

Intermediate 4

2-(1-Isopropyl-piperidin-4-yloxy)-4,5,6,7-tetrahydro-thieno[3,2-c]pyridine

In analogy to the procedure described for the synthesis of 2-(3-piperidin-1-yl-propoxy)-4,5,6,7-tetrahydro-thieno[3,2-c]pyridine (intermediate 1) the title compound was prepared from 5-trityl-5,6,7,7a-tetrahydro-4H-thieno[3,2-c]pyridin-2-one (FR 2576901 A1) and 4-bromo-1-isopropyl-piperidine (commercially available). The trityl-group was subsequently cleaved with TFA.

Intermediate 5

2-(1-Isopropyl-pyrrolidin-3-yloxy)-4,5,6,7-tetrahydro-thieno[3,2-c]pyridine

In analogy to the procedure described for the synthesis of 2-(3-piperidin-1-yl-propoxy)-4,5,6,7-tetrahydro-thieno[3,2-c]pyridine (intermediate 1) the title compound was prepared from 5-trityl-5,6,7,7a-tetrahydro-4H-thieno[3,2-c]pyridin-2-one (FR 2576901 A1) and 3-bromo-1-isopropyl-pyrrolidine (commercially available). The trityl group was subsequently cleaved with TFA.

Intermediate 6

2-(3-Morpholin-4-yl-propoxy)-4,5,6,7-tetrahydro-thieno[3,2-c]pyridine

In analogy to the procedure described for the synthesis of 2-(3-piperidin-1-yl-propoxy)-4,5,6,7-tetrahydro-thieno[3,2-c]pyridine (intermediate 1) the title compound was prepared from 5-trityl-5,6,7,7a-tetrahydro-4H-thieno[3,2-c]pyridin-2-one (FR 2576901 A1) and 4-(3-chloro-propyl)-morpholine (commercially available). The trityl-group was subsequently cleaved with TFA.

Intermediate 7

4-Methoxy-piperidine-1-carbonyl chloride

To a stirred solution of triphosgene (7.4 g, 0.025 mmol) in dichloromethane (200 ml) at ice bath was added dropwise a solution of 4-methoxy-piperidine hydrochloride salt (10 g, 0.066 mmol) and pyridine (10.9 g, 0.139 mmol) in dichloromethane (100 ml). The mixture was stirred over night and filtered through a silica pad, eluting with dichloromethane and evaporated. After trituration with diisopropyl ether, the mixture was used without purification.

Intermediate 8

N-Pentylcarbamoyl chloride

In analogy to the procedure described for the synthesis of 4-methoxy-piperidine-1-carbonyl chloride (intermediate 7) the title compound was prepared from triphosgene and pentylamine (commercially available).

Intermediate 9

N-Phenethyl-carbamoyl chloride

In analogy to the procedure described for the synthesis of 4-methoxy-piperidine-1-carbonyl chloride (intermediate 7) the title compound was prepared from triphosgene and phenethylamine (commercially available).

Intermediate 10

N-Phenpropyl-carbamoyl chloride

In analogy to the procedure described for the synthesis of 4-methoxy-piperidine-1-carbonyl chloride (intermediate 7) the title compound was prepared from triphosgene and phenpropylamine (commercially available).

Intermediate 11

4-Phenyl-piperidine-1-carbonyl chloride

In analogy to the procedure described for the synthesis of 4-methoxy-piperidine-1-carbonyl chloride (intermediate 7) the title compound was prepared from triphosgene and 4-phenyl-piperidine (commercially available).

Intermediate 12

4-(3,4-Dimethylphenyl)piperazine carbonyl chloride

In analogy to the procedure described for the synthesis of 4-methoxy-piperidine-1-carbonyl chloride (intermediate 7) the title compound was prepared from triphosgene and 4-phenyl-piperidine (commercially available).

Intermediate 13

N-(3-Methoxypropyl)carbamoyl chloride

In analogy to the procedure described for the synthesis of 4-methoxy-piperidine-1-carbonyl chloride (intermediate 7) the title compound was prepared from triphosgene and 3-methoxypropyl amine (commercially available).

Example 1

Morpholin-4-yl-[2-(3-piperidin-1-yl-propoxy)-6,7-dihydro-4H-thieno[3,2-c]pyridin-5-yl]-methanone A mixture of 120 mg (0.428 mmol) 2-(3-piperidin-1-yl-propoxy)-4,5,6,7-tetrahydro-thieno[3,2-c]pyridine (intermediate 1), 64 mg (0.428 mmol) of morpholine-4-carbonyl chloride (commercially available) and 108 mg (0.107 mmol) of triethyl amine in 10 mL DCM was stirred at room temperature overnight. After concentration in vacuo, the residue was purified by preparative TLC to give 79 mg of the product as white powder (42.8% yield). MS (m/e): 394.1 (MH$^+$).

In analogy to the procedure described for the synthesis of morpholin-4-yl-[2-(3-piperidin-1-yl-propoxy)-6,7-dihydro-4H-thieno[3,2-c]pyridin-5-yl]-methanone (example 1) further 6,7-dihydro-4H-thieno[3,2-c]pyridine derivatives have been synthesized from their respective starting materials mentioned in table 1. The purification was alternatively performed by preparative reversed phase HPLC. The examples are shown in table 1 and comprise example 2 to example 105.

TABLE 1

| No | MW | Name | Starting material | MW found [MH$^+$] |
|---|---|---|---|---|
| 2 | 391.58 | piperidin-1-yl-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and piperidinecarbonyl chloride (commercially available) | 392.2 |
| 3 | 377.55 | [2-(3-piperidin-1-yl-propoxy)-6,7-dihydro-4H-thieno[3,2-c]pyridin-5-yl]-pyrrolidin-1-yl-methanone | 2-(3-piperidin-1-yl-propoxy)-4,5,6,7-tetrahydro-thieno[3,2-c]pyridine (intermediate 1) and 1-pyrrolidinecarbonyl chloride (commercially available) | 378.1 |
| 4 | 406.59 | (4-methyl-piperazin-1-yl)-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 4-methylpiperazine-1-carbonyl chloride (commercially available) | 407.1 |
| 5 | 421.6 | (4-methoxy-piperidin-1-yl)-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 4-methoxy-piperidine-1-carbonyl chloride (intermediate 7) | 422.1 |
| 6 | 379.57 | 2-(3-piperidin-1-yl-propoxy)-6,7-dihydro-4H-thieno[3,2-c]pyridine-5-carboxylic acid diethylamide | 2-(3-piperidin-1-yl-propoxy)-4,5,6,7-tetrahydro-thieno[3,2-c]pyridine (intermediate 1) and diethyl carbamoyl chloride (commercially available) | 380.1 |
| 7 | 482.69 | [2-(3-piperidin-1-yl-propoxy)-6,7-dihydro-4H-thieno[3,2-c]pyridin-5-yl]-(4-o-tolyl-piperazin-1-yl)-methanone | 2-(3-piperidin-1-yl-propoxy)-4,5,6,7-tetrahydro-thieno[3,2-c]pyridine (intermediate 1) and 4-o-tolyl-piperazine-1-carbonyl chloride (prepared as in WO 9602525 A1) | 483.2 |
| 8 | 351.51 | 2-(3-piperidin-1-yl-propoxy)-6,7-dihydro-4H-thieno[3,2-c]pyridine-5-carboxylic acid ethylamide | 2-(3-piperidin-1-yl-propoxy)-4,5,6,7-tetrahydro-thieno[3,2-c]pyridine (intermediate 1) and ethyl isocyanate (commercially available) | 352.1 |
| 9 | 365.54 | 2-(3-piperidin-1-yl-propoxy)-6,7-dihydro-4H-thieno[3,2-c]pyridine-5-carboxylic acid isopropylamide | 2-(3-piperidin-1-yl-propoxy)-4,5,6,7-tetrahydro-thieno[3,2-c]pyridine (intermediate 1) and isopropyl isocyanate (commercially available) | 366.1 |
| 10 | 379.57 | 2-(3-piperidin-1-yl-propoxy)-6,7-dihydro-4H-thieno[3,2-c]pyridine-5-carboxylic acid isobutylamide | 2-(3-piperidin-1-yl-propoxy)-4,5,6,7-tetrahydro-thieno[3,2-c]pyridine (intermediate 1) and isobutyl carbamoyl chloride (prepared as in DE 2156761) | 380.1 |
| 11 | 393.59 | 2-(3-piperidin-1-yl-propoxy)-6,7-dihydro-4H-thieno[3,2-c]pyridine-5-carboxylic acid pentylamide | 2-(3-piperidin-1-yl-propoxy)-4,5,6,7-tetrahydro-thieno[3,2-c]pyridine (intermediate 1) and N-pentyl carbamoyl chloride (intermediate 8) | 394.1 |
| 12 | 407.62 | 2-(3-piperidin-1-yl-propoxy)-6,7-dihydro-4H-thieno[3,2-c]pyridine-5-carboxylic acid hexylamide | 2-(3-piperidin-1-yl-propoxy)-4,5,6,7-tetrahydro-thieno[3,2-c]pyridine (intermediate 1) and hexyl carbamoyl chloride (prepared as in FR 2406627) | 408.2 |

TABLE 1-continued

| No | MW | Name | Starting material | MW found [MH+] |
|---|---|---|---|---|
| 13 | 413.58 | 2-(3-piperidin-1-yl-propoxy)-6,7-dihydro-4H-thieno[3,2-c]pyridine-5-carboxylic acid benzylamide | 2-(3-piperidin-1-yl-propoxy)-4,5,6,7-tetrahydro-thieno[3,2-c]pyridine (intermediate 1) and 1-benzylcarbamoyl chloride (prepared as in DE 2210285) | 414.1 |
| 14 | 427.61 | 2-(3-piperidin-1-yl-propoxy)-6,7-dihydro-4H-thieno[3,2-c]pyridine-5-carboxylic acid phenethyl-amide | 2-(3-piperidin-1-yl-propoxy)-4,5,6,7-tetrahydro-thieno[3,2-c]pyridine (intermediate 1) and N-phenethyl carbamoyl chloride (intermediate 9) | 428.1 |
| 15 | 441.64 | 2-(3-piperidin-1-yl-propoxy)-6,7-dihydro-4H-thieno[3,2-c]pyridine-5-carboxylic acid (3-phenyl-propyl)-amide | 2-(3-piperidin-1-yl-propoxy)-4,5,6,7-tetrahydro-thieno[3,2-c]pyridine (intermediate 1) and N-phenpropyl carbamoyl chloride (intermediate 10) | 442.1 |
| 16 | 467.67 | (4-phenyl-piperidin-1-yl)-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 4-phenyl-piperidine-1-carbonyl chloride (intermediate 11) | 468.1 |
| 17 | 498.69 | [4-(2-methoxy-phenyl)-piperazin-1-yl]-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 4-(2-methoxy-phenyl)-piperazine-1-carbonyl chloride (prepared as in WO 9602525A1) | 499.1 |
| 18 | 381.54 | 2-(3-piperidin-1-yl-propoxy)-6,7-dihydro-4H-thieno[3,2-c]pyridine-5-carboxylic acid (2-methoxy-ethyl)-amide | 2-(3-piperidin-1-yl-propoxy)-4,5,6,7-tetrahydro-thieno[3,2-c]pyridine (intermediate 1) and 2-methoxyethylamine carbamoyl chloride (prepared as in EP 498334 A1) | 382.1 |
| 19 | 496.72 | [4-(3,4-dimethyl-phenyl)-piperazin-1-yl]-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 4-(3,4-dimethylphenyl) piperazine carbonyl chloride (intermediate 12) | 497.2 |
| 20 | 468.66 | (4-phenyl-piperazin-1-yl)-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 4-phenyl-piperazine-1-carbonyl chloride (prepared as in GB 2069497 A) | 469.1 |
| 21 | 486.65 | [4-(4-fluoro-phenyl)-piperazin-1-yl]-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 4-(4-fluoro-phenyl)-piperazine-1-carbonyl chloride (prepared as in GB 2069497 A) | 487.1 |
| 22 | 503.11 | [4-(4-chloro-phenyl)-piperazin-1-yl]-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 4-(4-chloro-phenyl)-piperazine-1-carbonyl chloride (WO 2004033463 A1) | 503 |
| 23 | 420.6 | 5-benzenesulfonyl-2-(3-piperidin-1-yl-propoxy)-4,5,6,7-tetrahydro-thieno[3,2-c]pyridine | 2-(3-piperidin-1-yl-propoxy)-4,5,6,7-tetrahydro-thieno[3,2-c]pyridine (intermediate 1) and benzenesulfonyl chloride (commercially available) | 421.1 |
| 24 | 434.62 | 2-(3-piperidin-1-yl-propoxy)-5-(toluene-4-sulfonyl)-4,5,6,7-tetrahydro-thieno[3,2-c]pyridine | 2-(3-piperidin-1-yl-propoxy)-4,5,6,7-tetrahydro-thieno[3,2-c]pyridine (intermediate 1) and 4-methyl-benzenesulfonyl chloride (commercially available) | 435.1 |
| 25 | 434.62 | 2-(3-piperidin-1-yl-propoxy)-5-(toluene-2-sulfonyl)-4,5,6,7-tetrahydro-thieno[3,2-c]pyridine | 2-(3-piperidin-1-yl-propoxy)-4,5,6,7-tetrahydro-thieno[3,2-c]pyridine (intermediate 1) and 2-methyl-benzenesulfonyl chloride (commercially available) | 435.1 |

TABLE 1-continued

| No | MW | Name | Starting material | MW found [MH+] |
|---|---|---|---|---|
| 26 | 372.55 | 5-ethanesulfonyl-2-(3-piperidin-1-yl-propoxy)-4,5,6,7-tetrahydro-thieno[3,2-c]pyridine | 2-(3-piperidin-1-yl-propoxy)-4,5,6,7-tetrahydro-thieno[3,2-c]pyridine (intermediate 1) and ethanesulfonyl chloride (commercially available) | 373.2 |
| 27 | 386.58 | 2-(3-piperidin-1-yl-propoxy)-5-(propane-2-sulfonyl)-4,5,6,7-tetrahydro-thieno[3,2-c]pyridine | 2-(3-piperidin-1-yl-propoxy)-4,5,6,7-tetrahydro-thieno[3,2-c]pyridine (intermediate 1) and propane-2-sulfonyl chloride (commercially available) | 387.2 |
| 28 | 400.61 | 5-(butane-1-sulfonyl)-2-(3-piperidin-1-yl-propoxy)-4,5,6,7-tetrahydro-thieno[3,2-c]pyridine | 2-(3-piperidin-1-yl-propoxy)-4,5,6,7-tetrahydro-thieno[3,2-c]pyridine (intermediate 1) and butane-1-sulfonyl chloride (commercially available) | 401.1 |
| 29 | 358.52 | 5-methanesulfonyl-2-(3-piperidin-1-yl-propoxy)-4,5,6,7-tetrahydro-thieno[3,2-c]pyridine | 2-(3-piperidin-1-yl-propoxy)-4,5,6,7-tetrahydro-thieno[3,2-c]pyridine (intermediate 1) and methanesulfonyl chloride (commercially available) | 359.1 |
| 30 | 418.64 | 2-(4-methyl-cyclohexyl)-1-[2-(3-piperidin-1-yl-propoxy)-6,7-dihydro-4H-thieno[3,2-c]pyridin-5-yl]-ethanone | 2-(3-piperidin-1-yl-propoxy)-4,5,6,7-tetrahydro-thieno[3,2-c]pyridine (intermediate 1) and (4-methyl-cyclohexyl)-acetyl chloride (DE 3219244 A1) | 419.3 |
| 31 | 420.52 | (2,3-difluoro-phenyl)-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 2,3-difluoro-benzoyl chloride (commercially available) | 421.2 |
| 32 | 364.55 | 3-methyl-1-[2-(3-piperidin-1-yl-propoxy)-6,7-dihydro-4H-thieno[3,2-c]pyridin-5-yl]-butan-1-one | 2-(3-piperidin-1-yl-propoxy)-4,5,6,7-tetrahydro-thieno[3,2-c]pyridine (intermediate 1) and 3-methyl-butyryl chloride (commercially available) | 365.2 |
| 33 | 350.52 | 1-[2-(3-piperidin-1-yl-propoxy)-6,7-dihydro-4H-thieno[3,2-c]pyridin-5-yl]-butan-1-one | 2-(3-piperidin-1-yl-propoxy)-4,5,6,7-tetrahydro-thieno[3,2-c]pyridine (intermediate 1) and butyryl chloride (commercially available) | 351.1 |
| 34 | 418.99 | (2-chloro-phenyl)-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 2-chloro-benzoyl chloride (commercially available) | 419 |
| 35 | 418.99 | (3-chloro-phenyl)-[2-(3-piperidin-1-yl-propoxy)-6,7-dihydro-4H-thieno[3,2-c]pyridin-5-yl]-methanone | 2-(3-piperidin-1-yl-propoxy)-4,5,6,7-tetrahydro-thieno[3,2-c]pyridine (intermediate 1) and 3-chloro-benzoyl chloride (commercially available) | 419 |
| 36 | 378.58 | 2-ethyl-1-[2-(3-piperidin-1-yl-propoxy)-6,7-dihydro-4H-thieno[3,2-c]pyridin-5-yl]-butan-1-one | 2-(3-piperidin-1-yl-propoxy)-4,5,6,7-tetrahydro-thieno[3,2-c]pyridine (intermediate 1) and 2-ethyl-butyryl chloride (commercially available) | 379.1 |
| 37 | 379.52 | morpholin-4-yl-[2-(3-pyrrolidin-1-yl-propoxy)-6,7-dihydro-4H-thieno[3,2-c]pyridin-5-yl]-methanone | 2-(3-pyrrolidin-1-yl-propoxy)-4,5,6,7-tetrahydro-thieno[3,2-c]pyridine (intermediate 2) and 4-morpholinyl carbonyl chloride (commercially available) | 380.2 |
| 38 | 377.55 | piperidin-1-yl-[2-(3-pyrrolidin-1-yl-propoxy)-6,7-dihydro-4H-thieno[3,2-c]pyridin-5-yl]-methanone | 2-(3-pyrrolidin-1-yl-propoxy)-4,5,6,7-tetrahydro-thieno[3,2-c]pyridine (intermediate 2) and piperidinecarbonyl chloride (commercially available) | 378.2 |
| 39 | 363.52 | pyrrolidin-1-yl-[2-(3-pyrrolidin-1-yl-propoxy)-6,7-dihydro-4H-thieno[3,2-c]pyridin-5-yl]-methanone | 2-(3-pyrrolidin-1-yl-propoxy)-4,5,6,7-tetrahydro-thieno[3,2-c]pyridine (intermediate 2) and 1-pyrrolidinecarbonyl chloride (commercially available) | 364.2 |

TABLE 1-continued

| No | MW | Name | Starting material | MW found [MH+] |
|---|---|---|---|---|
| 40 | 407.58 | (4-methoxy-piperidin-1-yl)-[2-(3-pyrrolidin-1-yl-propoxy)-6,7-dihydro-4H-thieno[3,2-c]pyridin-5-yl]-methanone | 2-(3-pyrrolidin-1-yl-propoxy)-4,5,6,7-tetrahydro-thieno[3,2-c]pyridine (intermediate 2) and 4-methoxy-piperidine-1-carbonyl chloride (intermediate 7) | 408.1 |
| 41 | 392.57 | (4-methyl-piperazin-1-yl)-[2-(3-pyrrolidin-1-yl-propoxy)-6,7-dihydro-4H-thieno[3,2-c]pyridin-5-yl]-methanone | 2-(3-pyrrolidin-1-yl-propoxy)-4,5,6,7-tetrahydro-thieno[3,2-c]pyridine (intermediate 2) and 4-methylpiperazine-1-carbonyl chloride (commercially available) | 393.1 |
| 42 | 337.49 | 2-(3-pyrrolidin-1-yl-propoxy)-6,7-dihydro-4H-thieno[3,2-c]pyridine-5-carboxylic acid ethylamide | 2-(3-pyrrolidin-1-yl-propoxy)-4,5,6,7-tetrahydro-thieno[3,2-c]pyridine (intermediate 2) and ethyl isocyanate (commercially available) | 338.1 |
| 43 | 351.51 | 2-(3-pyrrolidin-1-yl-propoxy)-6,7-dihydro-4H-thieno[3,2-c]pyridine-5-carboxylic acid isopropylamide | 2-(3-pyrrolidin-1-yl-propoxy)-4,5,6,7-tetrahydro-thieno[3,2-c]pyridine (intermediate 2) and isopropyl isocyanate (commercially available) | 352.1 |
| 44 | 365.54 | 2-(3-pyrrolidin-1-yl-propoxy)-6,7-dihydro-4H-thieno[3,2-c]pyridine-5-carboxylic acid isobutyl-amide | 2-(3-pyrrolidin-1-yl-propoxy)-4,5,6,7-tetrahydro-thieno[3,2-c]pyridine (intermediate 2) and isobutyl carbamoyl chloride (prepared as in DE 2156761) | 366.1 |
| 45 | 379.57 | 2-(3-pyrrolidin-1-yl-propoxy)-6,7-dihydro-4H-thieno[3,2-c]pyridine-5-carboxylic acid pentylamide | 2-(3-pyrrolidin-1-yl-propoxy)-4,5,6,7-tetrahydro-thieno[3,2-c]pyridine (intermediate 2) and N-pentyl carbamoyl chloride (intermediate 8) | 380.1 |
| 46 | 393.59 | 2-(3-pyrrolidin-1-yl-propoxy)-6,7-dihydro-4H-thieno[3,2-c]pyridine-5-carboxylic acid hexylamide | 2-(3-pyrrolidin-1-yl-propoxy)-4,5,6,7-tetrahydro-thieno[3,2-c]pyridine (intermediate 2) and hexyl carbamoyl chloride (prepared as in FR 2406627) | 394.1 |
| 47 | 381.54 | 2-(3-pyrrolidin-1-yl-propoxy)-6,7-dihydro-4H-thieno[3,2-c]pyridine-5-carboxylic acid (3-methoxy-propyl)-amide | 2-(3-pyrrolidin-1-yl-propoxy)-4,5,6,7-tetrahydro-thieno[3,2-c]pyridine (intermediate 2) and N-(3-methoxypropyl) carbamoyl chloride (intermediate 13) | 382.1 |
| 48 | 399.56 | 2-(3-pyrrolidin-1-yl-propoxy)-6,7-dihydro-4H-thieno[3,2-c]pyridine-5-carboxylic acid benzylamide | 2-(3-pyrrolidin-1-yl-propoxy)-4,5,6,7-tetrahydro-thieno[3,2-c]pyridine (intermediate 2) and 1-benzylcarbamoyl chloride (prepared as in DE 2210285) | 400.0 |
| 49 | 413.58 | 2-(3-pyrrolidin-1-yl-propoxy)-6,7-dihydro-4H-thieno[3,2-c]pyridine-5-carboxylic acid phenethyl-amide | 2-(3-pyrrolidin-1-yl-propoxy)-4,5,6,7-tetrahydro-thieno[3,2-c]pyridine (intermediate 2) and N-phenethyl carbamoyl chloride (intermediate 9) | 414.1 |
| 50 | 364.55 | 2-ethyl-1-[2-(3-pyrrolidin-1-yl-propoxy)-6,7-dihydro-4H-thieno[3,2-c]pyridin-5-yl]-butan-1-one | 2-(3-pyrrolidin-1-yl-propoxy)-4,5,6,7-tetrahydro-thieno[3,2-c]pyridine (intermediate 2) and 2-ethyl-butyryl chloride (commercially available) | 365.2 |
| 51 | 350.52 | 3-methyl-1-[2-(3-pyrrolidin-1-yl-propoxy)-6,7-dihydro-4H-thieno[3,2-c]pyridin-5-yl]-butan-1-one | 2-(3-pyrrolidin-1-yl-propoxy)-4,5,6,7-tetrahydro-thieno[3,2-c]pyridine (intermediate 2) and 3-methyl-butyryl chloride (commercially available) | 351.2 |
| 52 | 344.5 | 5-methanesulfonyl-2-(3-pyrrolidin-1-yl-propoxy)-4,5,6,7-tetrahydro-thieno[3,2-c]pyridine | 2-(3-pyrrolidin-1-yl-propoxy)-4,5,6,7-tetrahydro-thieno[3,2-c]pyridine (intermediate 2) and methanesulfonyl chloride (commercially available) | 345.1 |
| 53 | 386.58 | 5-(butane-1-sulfonyl)-2-(3-pyrrolidin-1-yl-propoxy)-4,5,6,7-tetrahydro-thieno[3,2-c]pyridine | 2-(3-pyrrolidin-1-yl-propoxy)-4,5,6,7-tetrahydro-thieno[3,2-c]pyridine (intermediate 2) and butane-1-sulfonyl chloride (commercially available) | 387.2 |

TABLE 1-continued

| No | MW | Name | Starting material | MW found [MH+] |
|---|---|---|---|---|
| 54 | 406.57 | 5-benzenesulfonyl-2-(3-pyrrolidin-1-yl-propoxy)-4,5,6,7-tetrahydro-thieno[3,2-c]pyridine | 2-(3-pyrrolidin-1-yl-propoxy)-4,5,6,7-tetrahydro-thieno[3,2-c]pyridine (intermediate 2) and benzenesulfonyl chloride (commercially available) | 407.1 |
| 55 | 420.6 | 2-(3-pyrrolidin-1-yl-propoxy)-5-(toluene-4-sulfonyl)-4,5,6,7-tetrahydro-thieno[3,2-c]pyridine | 2-(3-pyrrolidin-1-yl-propoxy)-4,5,6,7-tetrahydro-thieno[3,2-c]pyridine (intermediate 2) and 4-methyl-benzenesulfonyl chloride (commercially available) | 421.2 |
| 56 | 420.6 | 2-(3-pyrrolidin-1-yl-propoxy)-5-(toluene-2-sulfonyl)-4,5,6,7-tetrahydro-thieno[3,2-c]pyridine | 2-(3-pyrrolidin-1-yl-propoxy)-4,5,6,7-tetrahydro-thieno[3,2-c]pyridine (intermediate 2) and 2-methyl-benzenesulfonyl chloride (commercially available) | 421.2 |
| 57 | 420.6 | 2-(3-pyrrolidin-1-yl-propoxy)-5-(toluene-3-sulfonyl)-4,5,6,7-tetrahydro-thieno[3,2-c]pyridine | 2-(3-pyrrolidin-1-yl-propoxy)-4,5,6,7-tetrahydro-thieno[3,2-c]pyridine (intermediate 2) and 3-methyl-benzenesulfonyl chloride (commercially available) | 421.2 |
| 58 | 434.62 | 5-(4-ethyl-benzenesulfonyl)-2-(3-pyrrolidin-1-yl-propoxy)-4,5,6,7-tetrahydro-thieno[3,2-c]pyridine | 2-(3-pyrrolidin-1-yl-propoxy)-4,5,6,7-tetrahydro-thieno[3,2-c]pyridine (intermediate 2) and 4-ethyl-benzenesulfonyl chloride (commercially available) | 435.2 |
| 59 | 427.61 | 2-(3-pyrrolidin-1-yl-propoxy)-6,7-dihydro-4H-thieno[3,2-c]pyridine-5-carboxylic acid (3-phenyl-propyl)-amide | 2-(3-pyrrolidin-1-yl-propoxy)-4,5,6,7-tetrahydro-thieno[3,2-c]pyridine (intermediate 2) and N-phenpropyl carbamoyl chloride (intermediate 10) | 428.1 |
| 60 | 453.65 | (4-phenyl-piperidin-1-yl)-[2-(3-pyrrolidin-1-yl-propoxy)-6,7-dihydro-4H-thieno[3,2-c]pyridin-5-yl]-methanone | 2-(3-pyrrolidin-1-yl-propoxy)-4,5,6,7-tetrahydro-thieno[3,2-c]pyridine (intermediate 2) and 4-phenyl-piperidine-1-carbonyl chloride (intermediate 11) | 454.1 |
| 61 | 484.66 | [4-(2-methoxy-phenyl)-piperazin-1-yl]-[2-(3-pyrrolidin-1-yl-propoxy)-6,7-dihydro-4H-thieno[3,2-c]pyridin-5-yl]-methanone | 2-(3-pyrrolidin-1-yl-propoxy)-4,5,6,7-tetrahydro-thieno[3,2-c]pyridine (intermediate 2) and 4-(2-methoxy-phenyl)-piperazine-1-carbonyl chloride (prepared as in WO 9602525 A1) | 485.1 |
| 62 | 454.64 | (4-phenyl-piperazin-1-yl)-[2-(3-pyrrolidin-1-yl-propoxy)-6,7-dihydro-4H-thieno[3,2-c]pyridin-5-yl]-methanone | 2-(3-pyrrolidin-1-yl-propoxy)-4,5,6,7-tetrahydro-thieno[3,2-c]pyridine (intermediate 2) and 4-phenyl-piperazine-1-carbonyl chloride (prepared as in GB°2069497 A) | 455.1 |
| 63 | 367.51 | 2-(3-pyrrolidin-1-yl-propoxy)-6,7-dihydro-4H-thieno[3,2-c]pyridine-5-carboxylic acid (2-methoxy-ethyl)-amide | 2-(3-pyrrolidin-1-yl-propoxy)-4,5,6,7-tetrahydro-thieno[3,2-c]pyridine (intermediate 2) and 2-methoxyethylamine carbamoyl chloride (prepared as in EP 498334 A1) | 368.1 |
| 64 | 434.62 | 5-benzenesulfonyl-2-(1-isobutyl-piperidin-4-yloxy)-4,5,6,7-tetrahydro-thieno[3,2-c]pyridine | 2-(1-isobutyl-piperidin-4-yloxy)-4,5,6,7-tetrahydro-thieno[3,2-c]pyridine (intermediate 3) and benzenesulfonyl chloride (commercially available) | 435.2 |
| 65 | 448.65 | 2-(1-isobutyl-piperidin-4-yloxy)-5-(toluene-4-sulfonyl)-4,5,6,7-tetrahydro-thieno[3,2-c]pyridine | 2-(1-isobutyl-piperidin-4-yloxy)-4,5,6,7-tetrahydro-thieno[3,2-c]pyridine (intermediate 3) and 4-methyl-benzenesulfonyl chloride (commercially available) | 449.2 |
| 66 | 448.65 | 2-(1-isobutyl-piperidin-4-yloxy)-5-(toluene-2-sulfonyl)-4,5,6,7-tetrahydro-thieno[3,2- | 2-(1-isobutyl-piperidin-4-yloxy)-4,5,6,7-tetrahydro-thieno[3,2-c]pyridine (intermediate 3) and | 449.2 |

TABLE 1-continued

| No | MW | Name | Starting material | MW found [MH+] |
|---|---|---|---|---|
|  |  | c]pyridine | 2-methyl-benzenesulfonyl chloride (commercially available) |  |
| 67 | 448.65 | 2-(1-isobutyl-piperidin-4-yloxy)-5-(toluene-3-sulfonyl)-4,5,6,7-tetrahydro-thieno[3,2-c]pyridine | 2-(1-isobutyl-piperidin-4-yloxy)-4,5,6,7-tetrahydro-thieno[3,2-c]pyridine (intermediate 3) and 3-methyl-benzenesulfonyl chloride (commercially available) | 449.2 |
| 68 | 433.01 | (2-chloro-phenyl)-[2-(1-isobutyl-piperidin-4-yloxy)-6,7-dihydro-4H-thieno[3,2-c]pyridin-5-yl]-methanone | 2-(1-isobutyl-piperidin-4-yloxy)-4,5,6,7-tetrahydro-thieno[3,2-c]pyridine (intermediate 3) and 2-chloro-benzoyl chloride (commercially available) | 433.0 |
| 69 | 433.01 | (3-chloro-phenyl)-[2-(1-isobutyl-piperidin-4-yloxy)-6,7-dihydro-4H-thieno[3,2-c]pyridin-5-yl]-methanone | 2-(1-isobutyl-piperidin-4-yloxy)-4,5,6,7-tetrahydro-thieno[3,2-c]pyridine (intermediate 3) and 3-chloro-benzoyl chloride (commercially available) | 433.0 |
| 70 | 372.55 | 2-(1-isobutyl-piperidin-4-yloxy)-5-methanesulfonyl-4,5,6,7-tetrahydro-thieno[3,2-c]pyridine | 2-(1-isobutyl-piperidin-4-yloxy)-4,5,6,7-tetrahydro-thieno[3,2-c]pyridine (intermediate 3) and methanesulfonyl chloride (commercially available) | 373.0 |
| 71 | 386.58 | 5-ethanesulfonyl-2-(1-isobutyl-piperidin-4-yloxy)-4,5,6,7-tetrahydro-thieno[3,2-c]pyridine | 2-(1-isobutyl-piperidin-4-yloxy)-4,5,6,7-tetrahydro-thieno[3,2-c]pyridine (intermediate 3) and ethanesulfonyl chloride (commercially available) | 387.1 |
| 72 | 434.55 | (2,3-difluoro-phenyl)-[2-(1-isobutyl-piperidin-4-yloxy)-6,7-dihydro-4H-thieno[3,2-c]pyridin-5-yl]-methanone | 2-(1-isobutyl-piperidin-4-yloxy)-4,5,6,7-tetrahydro-thieno[3,2-c]pyridine (intermediate 3) and 2,3-difluoro-benzoyl chloride (commercially available) | 435.3 |
| 73 | 393.55 | [2-(1-isopropyl-piperidin-4-yloxy)-6,7-dihydro-4H-thieno[3,2-c]pyridin-5-yl]-morpholin-4-yl-methanone | 2-(1-isopropyl-piperidin-4-yloxy)-4,5,6,7-tetrahydro-thieno[3,2-c]pyridine (intermediate 4) and 4-morpholinyl carbonyl chloride (commercially available) | 394.1 |
| 74 | 421.6 | [2-(1-isopropyl-piperidin-4-yloxy)-6,7-dihydro-4H-thieno[3,2-c]pyridin-5-yl]-(4-methoxy-piperidin-1-yl)-methanone | 2-(1-isopropyl-piperidin-4-yloxy)-4,5,6,7-tetrahydro-thieno[3,2-c]pyridine (intermediate 4) and 4-methoxy-piperidine-1-carbonyl chloride (intermediate 7) | 422.1 |
| 75 | 365.54 | 2-(1-isopropyl-piperidin-4-yloxy)-6,7-dihydro-4H-thieno[3,2-c]pyridine-5-carboxylic acid isopropylamide | 2-(1-isopropyl-piperidin-4-yloxy)-4,5,6,7-tetrahydro-thieno[3,2-c]pyridine (intermediate 4) and isopropyl isocyanate (commercially available) | 366.1 |
| 76 | 350.52 | 1-[2-(1-isopropyl-piperidin-4-yloxy)-6,7-dihydro-4H-thieno[3,2-c]pyridin-5-yl]-butan-1-one | 2-(1-isopropyl-piperidin-4-yloxy)-4,5,6,7-tetrahydro-thieno[3,2-c]pyridine (intermediate 4) and butyryl chloride (commercially available) | 351.1 |
| 77 | 364.55 | 1-[2-(1-isopropyl-piperidin-4-yloxy)-6,7-dihydro-4H-thieno[3,2-c]pyridin-5-yl]-pentan-1-one | 2-(1-isopropyl-piperidin-4-yloxy)-4,5,6,7-tetrahydro-thieno[3,2-c]pyridine (intermediate 4) and pentanoyl chloride (commercially available) | 365.1 |
| 78 | 418.64 | 1-[2-(1-isopropyl-piperidin-4-yloxy)-6,7-dihydro-4H-thieno[3,2- | 2-(1-isopropyl-piperidin-4-yloxy)-4,5,6,7-tetrahydro-thieno[3,2-c]pyridine | 419.1 |

TABLE 1-continued

| No | MW | Name | Starting material | MW found [MH+] |
|---|---|---|---|---|
|  |  | c]pyridin-5-yl]-2-(4-methyl-cyclohexyl)-ethanone | (intermediate 4) and (4-methyl-cyclohexyl)-acetyl chloride (DE 3219244 A1) |  |
| 79 | 418.99 | (2-chloro-phenyl)-[2-(1-isopropyl-piperidin-4-yloxy)-6,7-dihydro-4H-thieno[3,2-c]pyridin-5-yl]-methanone | 2-(1-isopropyl-piperidin-4-yloxy)-4,5,6,7-tetrahydro-thieno[3,2-c]pyridine (intermediate 4) and 2-chloro-benzoyl chloride (commercially available) | 419.0 |
| 80 | 358.52 | 2-(1-isopropyl-piperidin-4-yloxy)-5-methane-sulfonyl-4,5,6,7-tetrahydro-thieno[3,2-c]pyridine | 2-(1-isopropyl-piperidin-4-yloxy)-4,5,6,7-tetrahydro-thieno[3,2-c]pyridine (intermediate 4) and methanesulfonyl chloride (commercially available) | 359.1 |
| 81 | 400.61 | 5-(butane-1-sulfonyl)-2-(1-isopropyl-piperidin-4-yloxy)-4,5,6,7-tetrahydro-thieno[3,2-c]pyridine | 2-(1-isopropyl-piperidin-4-yloxy)-4,5,6,7-tetrahydro-thieno[3,2-c]pyridine (intermediate 4) and butane-1-sulfonyl chloride (commercially available) | 401.1 |
| 82 | 420.6 | 5-benzenesulfonyl-2-(1-isopropyl-piperidin-4-yloxy)-4,5,6,7-tetrahydro-thieno[3,2-c]pyridine | 2-(1-isopropyl-piperidin-4-yloxy)-4,5,6,7-tetrahydro-thieno[3,2-c]pyridine (intermediate 4) and benzenesulfonyl chloride (commercially available) | 421.0 |
| 83 | 434.62 | 2-(1-isopropyl-piperidin-4-yloxy)-5-(toluene-2-sulfonyl)-4,5,6,7-tetrahydro-thieno[3,2-c]pyridine | 2-(1-isopropyl-piperidin-4-yloxy)-4,5,6,7-tetrahydro-thieno[3,2-c]pyridine (intermediate 4) and 2-methyl-benzenesulfonyl chloride (commercially available) | 435.0 |
| 84 | 434.62 | 2-(1-isopropyl-piperidin-4-yloxy)-5-(toluene-3-sulfonyl)-4,5,6,7-tetrahydro-thieno[3,2-c]pyridine | 2-(1-isopropyl-piperidin-4-yloxy)-4,5,6,7-tetrahydro-thieno[3,2-c]pyridine (intermediate 4) and 3-methyl-benzenesulfonyl chloride (commercially available) | 435.0 |
| 85 | 434.62 | 2-(1-isopropyl-piperidin-4-yloxy)-5-(toluene-4-sulfonyl)-4,5,6,7-tetrahydro-thieno[3,2-c]pyridine | 2-(1-isopropyl-piperidin-4-yloxy)-4,5,6,7-tetrahydro-thieno[3,2-c]pyridine (intermediate 4) and 4-methyl-benzenesulfonyl chloride (commercially available) | 435.0 |
| 86 | 448.65 | 5-(4-ethyl-benzenesulfonyl)-2-(1-isopropyl-piperidin-4-yloxy)-4,5,6,7-tetrahydro-thieno[3,2-c]pyridine | 2-(1-isopropyl-piperidin-4-yloxy)-4,5,6,7-tetrahydro-thieno[3,2-c]pyridine (intermediate 4) and 4-ethyl-benzenesulfonyl chloride (commercially available) | 449.0 |
| 87 | 351.51 | 2-(1-isopropyl-pyrrolidin-3-yloxy)-6,7-dihydro-4H-thieno[3,2-c]pyridine-5-carboxylic acid isopropylamide | 2-(1-isopropyl-pyrrolidin-3-yloxy)-4,5,6,7-tetrahydro-thieno[3,2-c]pyridine (intermediate 5) and isopropyl isocyanate (commercially available) | 352.1 |
| 88 | 379.52 | [2-(1-isopropyl-pyrrolidin-3-yloxy)-6,7-dihydro-4H-thieno[3,2-c]pyridin-5-yl]-morpholin-4-yl-methanone | 2-(1-isopropyl-pyrrolidin-3-yloxy)-4,5,6,7-tetrahydro-thieno[3,2-c]pyridine (intermediate 5) and 4-morpholinyl carbonyl chloride (commercially available) | 380.0 |
| 89 | 364.55 | 2-ethyl-1-[2-(1-isopropyl-pyrrolidin-3-yloxy)-6,7-dihydro-4H-thieno[3,2-c]pyridin-5-yl]-butan-1-one | 2-(1-isopropyl-pyrrolidin-3-yloxy)-4,5,6,7-tetrahydro-thieno[3,2-c]pyridine (intermediate 5) and 2-ethyl-butyryl chloride (commercially available) | 365.1 |
| 90 | 404.62 | 1-[2-(1-isopropyl-pyrrolidin-3-yloxy)-6,7-dihydro-4H-thieno[3,2- | 2-(1-isopropyl-pyrrolidin-3-yloxy)-4,5,6,7-tetrahydro-thieno[3,2-c]pyridine | 405.2 |

TABLE 1-continued

| No | MW | Name | Starting material | MW found [MH$^+$] |
|---|---|---|---|---|
| | | c]pyridin-5-yl]-2-(4-methyl-cyclohexyl)-ethanone | (intermediate 5) and (4-methyl-cyclohexyl)-acetyl chloride (DE 3219244 A1) | |
| 91 | 404.96 | (2-chloro-phenyl)-[2-(1-isopropyl-pyrrolidin-3-yloxy)-6,7-dihydro-4H-thieno[3,2-c]pyridin-5-yl]-methanone | 2-(1-isopropyl-pyrrolidin-3-yloxy)-4,5,6,7-tetrahydro-thieno[3,2-c]pyridine (intermediate 5) and 2-chloro-benzoyl chloride (commercially available) | 405.0 |
| 92 | 404.96 | (3-chloro-phenyl)-[2-(1-isopropyl-pyrrolidin-3-yloxy)-6,7-dihydro-4H-thieno[3,2-c]pyridin-5-yl]-methanone | 2-(1-isopropyl-pyrrolidin-3-yloxy)-4,5,6,7-tetrahydro-thieno[3,2-c]pyridine (intermediate 5) and 3-chloro-benzoyl chloride (commercially available) | 405.0 |
| 93 | 406.5 | (2,3-difluoro-phenyl)-[2-(1-isopropyl-pyrrolidin-3-yloxy)-6,7-dihydro-4H-thieno[3,2-c]pyridin-5-yl]-methanone | 2-(1-isopropyl-pyrrolidin-3-yloxy)-4,5,6,7-tetrahydro-thieno[3,2-c]pyridine (intermediate 5) and 2,3-difluoro-benzoyl chloride (commercially available) | 407.1 |
| 94 | 363.52 | [2-(1-isopropyl-pyrrolidin-3-yloxy)-6,7-dihydro-4H-thieno[3,2-c]pyridin-5-yl]-pyrrolidin-1-yl-methanone | 2-(1-isopropyl-pyrrolidin-3-yloxy)-4,5,6,7-tetrahydro-thieno[3,2-c]pyridine (intermediate 5) and 1-pyrrolidinecarbonyl chloride (commercially available) | 364.1 |
| 95 | 350.52 | 1-[2-(1-isopropyl-pyrrolidin-3-yloxy)-6,7-dihydro-4H-thieno[3,2-c]pyridin-5-yl]-3-methyl-butan-1-one | 2-(1-isopropyl-pyrrolidin-3-yloxy)-4,5,6,7-tetrahydro-thieno[3,2-c]pyridine (intermediate 5) and 3-methyl-butyryl chloride (commercially available) | 351.1 |
| 96 | 344.5 | 2-(1-isopropyl-pyrrolidin-3-yloxy)-5-methane-sulfonyl-4,5,6,7-tetrahydro-thieno[3,2-c]pyridine | 2-(1-isopropyl-pyrrolidin-3-yloxy)-4,5,6,7-tetrahydro-thieno[3,2-c]pyridine (intermediate 5) and methanesulfonyl chloride (commercially available) | 345.0 |
| 97 | 406.57 | 5-benzenesulfonyl-2-(1-isopropyl-pyrrolidin-3-yloxy)-4,5,6,7-tetrahydro-thieno[3,2-c]pyridine | 2-(1-isopropyl-pyrrolidin-3-yloxy)-4,5,6,7-tetrahydro-thieno[3,2-c]pyridine (intermediate 5) and benzenesulfonyl chloride (commercially available) | 407.0 |
| 98 | 420.6 | 2-(1-isopropyl-pyrrolidin-3-yloxy)-5-(toluene-3-sulfonyl)-4,5,6,7-tetrahydro-thieno[3,2-c]pyridine | 2-(1-isopropyl-pyrrolidin-3-yloxy)-4,5,6,7-tetrahydro-thieno[3,2-c]pyridine (intermediate 5) and 3-methyl-benzenesulfonyl chloride (commercially available) | 421.0 |
| 99 | 434.62 | 5-(4-ethyl-benzenesulfonyl)-2-(1-isopropyl-pyrrolidin-3-yloxy)-4,5,6,7-tetrahydro-thieno[3,2-c]pyridine | 2-(1-isopropyl-pyrrolidin-3-yloxy)-4,5,6,7-tetrahydro-thieno[3,2-c]pyridine (intermediate 5) and 4-ethyl-benzenesulfonyl chloride (commercially available) | 435.1 |
| 100 | 372.55 | 2-(1-isopropyl-pyrrolidin-3-yloxy)-5-(propane-2-sulfonyl)-4,5,6,7-tetrahydro-thieno[3,2-c]pyridine | 2-(1-isopropyl-pyrrolidin-3-yloxy)-4,5,6,7-tetrahydro-thieno[3,2-c]pyridine (intermediate 5) and propane-2-sulfonyl chloride (commercially available) | 373.0 |
| 101 | 386.51 | [2-(3-morpholin-4-yl-propoxy)-6,7-dihydro-4H-thieno[3,2-c]pyridin-5-yl]-phenyl-methanone | 2-(3-morpholin-4-yl-propoxy)-4,5,6,7-tetrahydro-thieno[3,2-c]pyridine (intermediate 6) and benzoylchloride (commercially available) | 387.1 |
| 102 | 436.59 | 2-(3-morpholin-4-yl-propoxy)-5-(toluene-2-sulfonyl)-4,5,6,7-tetrahydro-thieno[3,2-c]pyridine | 2-(3-morpholin-4-yl-propoxy)-4,5,6,7-tetrahydro-thieno[3,2-c]pyridine (intermediate 6) and 2-methyl-benzenesulfonyl chloride (commercially available) | 437.0 |

TABLE 1-continued

| No | MW | Name | Starting material | MW found [MH$^+$] |
|---|---|---|---|---|
| 103 | 443.61 | 2-(3-morpholin-4-yl-propoxy)-6,7-dihydro-4H-thieno[3,2-c]pyridine-5-carboxylic acid (3-phenyl-propyl)-amide | 2-(3-morpholin-4-yl-propoxy)-4,5,6,7-tetrahydro-thieno[3,2-c]pyridine (intermediate 6) and N-phenpropyl carbamoyl chloride (intermediate 10) | 444.1 |
| 104 | 469.65 | [2-(3-morpholin-4-yl-propoxy)-6,7-dihydro-4H-thieno[3,2-c]pyridin-5-yl]-(4-phenyl-piperidin-1-yl)-methanone | 2-(3-morpholin-4-yl-propoxy)-4,5,6,7-tetrahydro-thieno[3,2-c]pyridine (intermediate 6) and 4-phenyl-piperidine-1-carbonyl chloride (intermediate 11) | 470.1 |
| 105 | 500.66 | [4-(4-methoxy-phenyl)-piperazin-1-yl]-[2-(3-morpholin-4-yl-propoxy)-6,7-dihydro-4H-thieno[3,2-c]pyridin-5-yl]-methanone | 2-(3-morpholin-4-yl-propoxy)-4,5,6,7-tetrahydro-thieno[3,2-c]pyridine (intermediate 6) and 4-(4-methoxy-phenyl)-piperazine-1-carbonyl chloride (prepared as in WO 2004033463 A1) | 501.1 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

It is to be understood that the invention is not limited to the particular embodiments of the invention described above, as variations of the particular embodiments may be made and still fall within the scope of the appended claims.

What is claimed is:

1. A compound of formula (I):

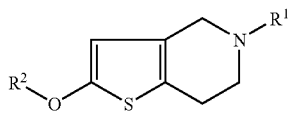

I

Wherein:
$R^1$ is selected from the group consisting of
—CO—$R^3$, wherein
$R^3$ is selected from the group consisting of
lower alkyl,
lower cycloalkylalkyl, wherein the cycloalkyl ring may be unsubstituted or substituted with one or two groups independently selected from lower alkyl, and
phenyl, wherein the phenyl ring may be unsubstituted or substituted with one or two groups independently selected from lower alkyl, cyano, halogen, lower halogenalkyl and lower alkoxy,
—CO—$NR^4R^5$, wherein
$R^4$ and $R^5$ independently from each other are selected from the group consisting of hydrogen, lower alkyl, lower alkoxyalkyl,
phenyl unsubstituted or substituted with one or two groups independently selected from lower alkyl, halogen, lower alkoxy and lower halogenalkyl, and
lower phenylalkyl, wherein phenyl is unsubstituted or substituted with one or two groups independently selected from lower alkyl, halogen, lower alkoxy and lower halogenalkyl,
or $R^4$ and $R^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy, and
—$SO_2$—$R^6$, wherein
$R^6$ is selected from the group consisting of
lower alkyl, lower alkoxyalkyl,
lower cycloalkylalkyl, wherein the cycloalkyl ring may be unsubstituted or substituted with one or two groups independently selected from lower alkyl, halogen and lower alkoxy, and
phenyl, wherein the phenyl ring may be unsubstituted or substituted with one or two groups independently selected from lower alkyl, cyano, halogen, lower halogenalkyl and lower alkoxy;
$R^2$ is a group selected from

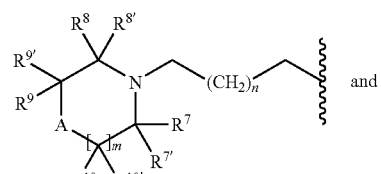

$R^{2a}$

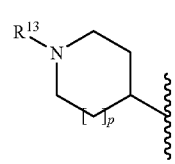

$R^{2b}$ wherein
m is 0, 1 or 2;
n is 0, 1 or 2;
A is selected from —$CR^{11}R^{11'}$—, O, S or —$NR^{12}$;
$R^7$, $R^{7'}$, $R^8$, $R^{8'}$, $R^9$, $R^{9'}$, $R^{10}$, $R^{10'}$, $R^{11}$ and $R^{11'}$ independently from each other are hydrogen or lower alkyl;
$R^{12}$ is hydrogen or lower alkyl;
p is 0, 1 or 2; and
$R^{13}$ is lower alkyl or cycloalkyl;
and pharmaceutically acceptable salts thereof.

2. The compound according to claim 1, wherein $R^1$ is —CO—$NR^4R^5$ and wherein $R^4$ and $R^5$ independently from each other are selected from the group consisting of
hydrogen, lower alkyl, lower alkoxyalkyl,
phenyl unsubstituted or substituted with one or two groups independently selected from lower alkyl, halogen, lower alkoxy and lower halogenalkyl, and
lower phenylalkyl, wherein phenyl is unsubstituted or substituted with one or two groups independently selected from lower alkyl, halogen, lower alkoxy and lower halogenalkyl, or $R^4$ and $R^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy.

3. The compound according to claim 1, wherein $R^1$ is —CO—$NR^4R^5$ and wherein $R^4$ and $R^5$ independently from each other are selected from the group consisting of
hydrogen, lower alkyl, lower alkoxyalkyl,
phenyl unsubstituted or substituted with one or two groups independently selected from lower alkyl, halogen, lower alkoxy and lower halogenalkyl, and
lower phenylalkyl, wherein phenyl is unsubstituted or substituted with one or two groups independently selected from lower alkyl, halogen, lower alkoxy and lower halogenalkyl.

4. The compound according to claim 1, wherein $R^1$ is —CO—$NR^4R^5$ and wherein $R^4$ and $R^5$ together with the nitrogen atom to which they are attached form a 4-, 5-, 6- or 7-membered heterocyclic ring optionally containing a further heteroatom selected from nitrogen, oxygen or sulfur, a sulfinyl group or a sulfonyl group, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy.

5. The compound according to claim 1, wherein $R^1$ is $-CO-NR^4R^5$ and wherein $R^4$ and $R^5$ together with the nitrogen atom to which they are attached form a heterocyclic ring selected from the group consisting of pyrrolidinyl, piperidinyl, piperazinyl and morpholinyl, said heterocyclic ring being unsubstituted or substituted with one or two groups independently selected from lower alkyl, halogen, cyano, lower alkoxy and phenyl, wherein phenyl is unsubstituted or substituted with one or two groups independently selected from lower alkyl, halogen and lower alkoxy.

6. The compound according to claim 1, wherein $R^1$ is $-CO-R^3$ and wherein $R^3$ is selected from the group consisting of lower alkyl, lower cycloalkylalkyl, wherein the cycloalkyl ring may be unsubstituted or substituted with one or two groups independently selected from lower alkyl, and phenyl, wherein the phenyl ring may be unsubstituted or substituted with one or two groups independently selected from lower alkyl, cyano, halogen, lower halogenalkyl and lower alkoxy.

7. The compound according to claim 1, wherein $R^1$ is $-CO-R^3$ and wherein $R^3$ is lower alkyl or lower cycloalkylalkyl, wherein the cycloalkyl ring may be unsubstituted or substituted with one or two groups independently selected from lower alkyl.

8. The compound according to claim 1, wherein $R^1$ is $-CO-R^3$ and wherein $R^3$ is phenyl, wherein the phenyl ring may be unsubstituted or substituted with one or two groups independently selected from lower alkyl, cyano, halogen, lower halogenalkyl and lower alkoxy.

9. The compound according to claim 1, wherein $R^1$ is $SO_2-R^6$ and wherein $R^6$ is selected from the group consisting of lower alkyl, lower alkoxyalkyl,
   lower cycloalkylalkyl, wherein the cycloalkyl ring may be unsubstituted or substituted with one or two groups independently selected from lower alkyl, halogen and lower alkoxy, and
   phenyl, wherein the phenyl ring may be unsubstituted or substituted with one or two groups independently selected from lower alkyl, cyano, halogen, lower halogenalkyl and lower alkoxy.

10. The compound according to claim 1, wherein $R^1$ is $SO_2-R^6$ and wherein $R^6$ is lower alkyl or phenyl, wherein the phenyl ring may be unsubstituted or substituted with one or two lower alkyl groups.

11. The compound according to claim 1, wherein $R^2$ signifies

wherein
m is 0 or 1;
n is 1;
A is selected from $-CR^{11}R^{11'}-$, O, S or $-NR^{12}$;
$R^7$, $R^{7'}$, $R^8$, $R^{8'}$, $R^9$, $R^{9'}$, $R^{10}$, $R^{10'}$, $R^{11}$ and $R^{11'}$ independently from each other are hydrogen or lower alkyl; and
$R^{12}$ is hydrogen or lower alkyl.

12. Compounds of formula I according to any one of claims 1 to 11, wherein A is $CR^{11}R^{11'}$ and $R^7$, $R^{7'}$, $R^8$, $R^{8'}$, $R^9$, $R^{9'}$, $R^{10}$, $R^{10'}$, $R^{11}$ and $R^{11'}$ independently from each other are hydrogen or lower alkyl.

13. The compound according to claim 1, wherein $R^7$, $R^{7'}$, $R^8$, $R^{8'}$, $R^9$, $R^{9'}$, $R^{10}$, $R^{10'}$, $R^{11}$ and $R^{11'}$ are hydrogen.

14. The compound according to claim 1, wherein A is O and $R^7$, $R^{7'}$, $R^8$, $R^{8'}$, $R^9$, $R^{9'}$, $R^{10}$ and $R^{10'}$ are hydrogen.

15. The compound according to claim 1, wherein $R^2$ signifies

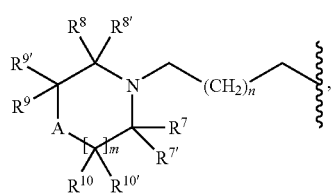

wherein p is 0, 1 or 2; and $R^{13}$ is lower alkyl or cycloalkyl.

16. The compound according to claim 1, wherein $R^{13}$ is isopropyl or isobutyl.

17. The compound according to claim 1, wherein p is 0 or 1.

18. The compound according to claim 1, selected from the group consisting of:
   morpholin-4-yl-[2-(3-piperidin-1-yl-propoxy)-6,7-dihydro-4H-thieno[3,2-c]pyridin-5-yl]-methanone, piperidin-1-yl-[2-(3-piperidin-1-yl-propoxy)-6,7-dihydro-4H-thieno[3,2-c]pyridin-5-yl]-methanone, [2-(3-piperidin-1-yl-propoxy)-6,7-dihydro-4H-thieno[3,2-c]pyridin-5-yl]-pyrrolidin-1-yl-methanone, (4-methyl-piperazin-1-yl)-[2-(3-piperidin-1-yl-propoxy)-6,7-dihydro-4H-thieno[3,2-c]pyridin-5-yl]-methanone, (4-methoxy-piperidin-1-yl)-[2-(3-piperidin-1-yl-propoxy)-6,7-dihydro-4H-thieno[3,2-c]pyridin-5-yl]-methanone,
   2-(3-piperidin-1-yl-propoxy)-6,7-dihydro-4H-thieno[3,2-c]pyridine-5-carboxylic acid diethylamide,
   [2-(3-piperidin-1-yl-propoxy)-6,7-dihydro-4H-thieno[3,2-c]pyridin-5-yl]-(4-o-tolyl-piperazin-1-yl)-methanone,
   2-(3-piperidin-1-yl-propoxy)-6,7-dihydro-4H-thieno[3,2-c]pyridine-5-carboxylic acid ethylamide,
   2-(3-piperidin-1-yl-propoxy)-6,7-dihydro-4H-thieno[3,2-c]pyridine-5-carboxylic acid isopropylamide,
   2-(3-piperidin-1-yl-propoxy)-6,7-dihydro-4H-thieno[3,2-c]pyridine-5-carboxylic acid isobutyl-amide,
   2-(3-piperidin-1-yl-propoxy)-6,7-dihydro-4H-thieno[3,2-c]pyridine-5-carboxylic acid pentylamide,
   2-(3-piperidin-1-yl-propoxy)-6,7-dihydro-4H-thieno[3,2-c]pyridine-5-carboxylic acid hexylamide,
   2-(3-piperidin-1-yl-propoxy)-6,7-dihydro-4H-thieno[3,2-c]pyridine-5-carboxylic acid benzylamide,
   2-(3-piperidin-1-yl-propoxy)-6,7-dihydro-4H-thieno[3,2-c]pyridine-5-carboxylic acid phenethyl-amide,
   2-(3-piperidin-1-yl-propoxy)-6,7-dihydro-4H-thieno[3,2-c]pyridine-5-carboxylic acid (3-phenyl-propyl)-amide, (4-phenyl-piperidin-1-yl)-[2-(3-piperidin-1-yl-propoxy)-6,7-dihydro-4H-thieno[3,2-c]pyridin-5-yl]-methanone,
[4-(2-methoxy-phenyl)-piperazin-1-yl]-[2-(3-piperidin-1-yl-propoxy)-6,7-dihydro-4H-thieno[3,2-c]pyridin-5-yl]-methanone,
2-(3-piperidin-1-yl-propoxy)-6,7-dihydro-4H-thieno[3,2-c]pyridine-5-carboxylic acid (2-methoxy-ethyl)-amide,
[4-(3,4-dimethyl-phenyl)-piperazin-1-yl]-[2-(3-piperidin-1-yl-propoxy)-6,7-dihydro-4H-thieno[3,2-c]pyridin-5-yl]-methanone,
(4-phenyl-piperazin-1-yl)-[2-(3-piperidin-1-yl-propoxy)-6,7-dihydro-4H-thieno[3,2-c]pyridin-5-yl]-methanone, and
[4-(4-fluoro-phenyl)-piperazin-1-yl]-[2-(3-piperidin-1-yl-propoxy)-6,7-dihydro-4H-thieno[3,2-c]pyridin-5-yl]-methanone.

19. The compound according to claim 1, selected from the group consisting of:
[4-(4-chloro-phenyl)-piperazin-1-yl]-[2-(3-piperidin-1-yl-propoxy)-6,7-dihydro-4H-thieno[3,2-c]pyridin-5-yl]-methanone,
5-benzenesulfonyl-2-(3-piperidin-1-yl-propoxy)-4,5,6,7-tetrahydro-thieno[3,2-c]pyridine,
2-(3-piperidin-1-yl-propoxy)-5-(toluene-4-sulfonyl)-4,5,6,7-tetrahydro-thieno[3,2-c]pyridine,
2-(3-piperidin-1-yl-propoxy)-5-(toluene-2-sulfonyl)-4,5,6,7-tetrahydro-thieno[3,2-c]pyridine,
5-ethanesulfonyl-2-(3-piperidin-1-yl-propoxy)-4,5,6,7-tetrahydro-thieno[3,2-c]pyridine,
2-(3-piperidin-1-yl-propoxy)-5-(propane-2-sulfonyl)-4,5,6,7-tetrahydro-thieno[3,2-c]pyridine,
5-(butane-1-sulfonyl)-2-(3-piperidin-1-yl-propoxy)-4,5,6,7-tetrahydro-thieno[3,2-c]pyridine,
5-methanesulfonyl-2-(3-piperidin-1-yl-propoxy)-4,5,6,7-tetrahydro-thieno[3,2-c]pyridine,
2-(4-methyl-cyclohexyl)-1-[2-(3-piperidin-1-yl-propoxy)-6,7-dihydro-4H-thieno[3,2-c]pyridin-5-yl]-ethanone,
(2,3-difluoro-phenyl)-[2-(3-piperidin-1-yl-propoxy)-6,7-dihydro-4H-thieno[3,2-c]pyridin-5-yl]-methanone,
3-methyl-1-[2-(3-piperidin-1-yl-propoxy)-6,7-dihydro-4H-thieno[3,2-c]pyridin-5-yl]-butan-1-one,
1-[2-(3-piperidin-1-yl-propoxy)-6,7-dihydro-4H-thieno[3,2-c]pyridin-5-yl]-butan-1-one,
(2-chloro-phenyl)-[2-(3-piperidin-1-yl-propoxy)-6,7-dihydro-4H-thieno[3,2-c]pyridin-5-yl]-methanone,
(3-chloro-phenyl)-[2-(3-piperidin-1-yl-propoxy)-6,7-dihydro-4H-thieno[3,2-c]pyridin-5-yl]-methanone,
2-ethyl-1-[2-(3-piperidin-1-yl-propoxy)-6,7-dihydro-4H-thieno[3,2-c]pyridin-5-yl]-butan-1-one,
morpholin-4-yl-[2-(3-pyrrolidin-1-yl-propoxy)-6,7-dihydro-4H-thieno[3,2-c]pyridin-5-yl]-methanone,
piperidin-1-yl-[2-(3-pyrrolidin-1-yl-propoxy)-6,7-dihydro-4H-thieno[3,2-c]pyridin-5-yl]-methanone,
pyrrolidin-1-yl-[2-(3-pyrrolidin-1-yl-propoxy)-6,7-dihydro-4H-thieno[3,2-c]pyridin-5-yl]-methanone,
(4-methoxy-piperidin-1-yl)-[2-(3-pyrrolidin-1-yl-propoxy)-6,7-dihydro-4H-thieno[3,2-c]pyridin-5-yl]-methanone, and
(4-methyl-piperazin-1-yl)-[2-(3-pyrrolidin-1-yl-propoxy)-6,7-dihydro-4H-thieno[3,2-c]pyridin-5-yl]-methanone.

20. The compound according to claim 1, selected from the group consisting of:
2-(3-pyrrolidin-1-yl-propoxy)-6,7-dihydro-4H-thieno[3,2-c]pyridine-5-carboxylic acid ethylamide,
2-(3-pyrrolidin-1-yl-propoxy)-6,7-dihydro-4H-thieno[3,2-c]pyridine-5-carboxylic acid isopropylamide,
2-(3-pyrrolidin-1-yl-propoxy)-6,7-dihydro-4H-thieno[3,2-c]pyridine-5-carboxylic acid isobutyl-amide,
2-(3-pyrrolidin-1-yl-propoxy)-6,7-dihydro-4H-thieno[3,2-c]pyridine-5-carboxylic acid pentylamide,
2-(3-pyrrolidin-1-yl-propoxy)-6,7-dihydro-4H-thieno[3,2-c]pyridine-5-carboxylic acid hexylamide,
2-(3-pyrrolidin-1-yl-propoxy)-6,7-dihydro-4H-thieno[3,2-c]pyridine-5-carboxylic acid (3-methoxy-propyl)-amide,
2-(3-pyrrolidin-1-yl-propoxy)-6,7-dihydro-4H-thieno[3,2-c]pyridine-5-carboxylic acid benzylamide,
2-(3-pyrrolidin-1-yl-propoxy)-6,7-dihydro-4H-thieno[3,2-c]pyridine-5-carboxylic acid phenethyl-amide,
2-ethyl-1-[2-(3-pyrrolidin-1-yl-propoxy)-6,7-dihydro-4H-thieno[3,2-c]pyridin-5-yl]-butan-1-one,
3-methyl-1-[2-(3-pyrrolidin-1-yl-propoxy)-6,7-dihydro-4H-thieno[3,2-c]pyridin-5-yl]-butan-1-one,
5-methanesulfonyl-2-(3-pyrrolidin-1-yl-propoxy)-4,5,6,7-tetrahydro-thieno[3,2-c]pyridine,
5-(butane-1-sulfonyl)-2-(3-pyrrolidin-1-yl-propoxy)-4,5,6,7-tetrahydro-thieno[3,2-c]pyridine,
5-benzenesulfonyl-2-(3-pyrrolidin-1-yl-propoxy)-4,5,6,7-tetrahydro-thieno[3,2-c]pyridine,
2-(3-pyrrolidin-1-yl-propoxy)-5-(toluene-4-sulfonyl)-4,5,6,7-tetrahydro-thieno[3,2-c]pyridine,
2-(3-pyrrolidin-1-yl-propoxy)-5-(toluene-2-sulfonyl)-4,5,6,7-tetrahydro-thieno[3,2-c]pyridine,
2-(3-pyrrolidin-1-yl-propoxy)-5-(toluene-3-sulfonyl)-4,5,6,7-tetrahydro-thieno[3,2-c]pyridine,
5-(4-ethyl-benzenesulfonyl)-2-(3-pyrrolidin-1-yl-propoxy)-4,5,6,7-tetrahydro-thieno[3,2-c]pyridine, and
2-(3-pyrrolidin-1-yl-propoxy)-6,7-dihydro-4H-thieno[3,2-c]pyridine-5-carboxylic acid (3-phenyl-propyl)-amide.

21. The compound according to claim 1, selected from the group consisting of:
(4-phenyl-piperidin-1-yl)-[2-(3-pyrrolidin-1-yl-propoxy)-6,7-dihydro-4H-thieno[3,2-c]pyridin-5-yl]-methanone,
[4-(2-methoxy-phenyl)-piperazin-1-yl]-[2-(3-pyrrolidin-1-yl-propoxy)-6,7-dihydro-4H-thieno[3,2-c]pyridin-5-yl]-methanone,
(4-phenyl-piperazin-1-yl)-[2-(3-pyrrolidin-1-yl-propoxy)-6,7-dihydro-4H-thieno[3,2-c]pyridin-5-yl]-methanone,
2-(3-pyrrolidin-1-yl-propoxy)-6,7-dihydro-4H-thieno[3,2-c]pyridine-5-carboxylic acid (2-methoxy-ethyl)-amide,
5-benzenesulfonyl-2-(1-isobutyl-piperidin-4-yloxy)-4,5,6,7-tetrahydro-thieno[3,2-c]pyridine,
2-(1-isobutyl-piperidin-4-yloxy)-5-(toluene-4-sulfonyl)-4,5,6,7-tetrahydro-thieno[3,2-c]pyridine,
2-(1-isobutyl-piperidin-4-yloxy)-5-(toluene-2-sulfonyl)-4,5,6,7-tetrahydro-thieno[3,2-c]pyridine,
2-(1-isobutyl-piperidin-4-yloxy)-5-(toluene-3-sulfonyl)-4,5,6,7-tetrahydro-thieno[3,2-c]pyridine,
(2-chloro-phenyl)-[2-(1-isobutyl-piperidin-4-yloxy)-6,7-dihydro-4H-thieno[3,2-c]pyridin-5-yl]-methanone,
(3-chloro-phenyl)-[2-(1-isobutyl-piperidin-4-yloxy)-6,7-dihydro-4H-thieno[3,2-c]pyridin-5-yl]-methanone,
2-(1-isobutyl-piperidin-4-yloxy)-5-methanesulfonyl-4,5,6,7-tetrahydro-thieno[3,2-c]pyridine,
5-ethanesulfonyl-2-(1-isobutyl-piperidin-4-yloxy)-4,5,6,7-tetrahydro-thieno[3,2-c]pyridine, (2,3-difluoro-phenyl)-[2-(1-isobutyl-piperidin-4-yloxy)-6,7-dihydro-4H-thieno[3,2-c]pyridin-5-yl]-methanone,
[2-(1-isopropyl-piperidin-4-yloxy)-6,7-dihydro-4H-thieno[3,2-c]pyridin-5-yl]-morpholin-4-yl-methanone,
[2-(1-isopropyl-piperidin-4-yloxy)-6,7-dihydro-4H-thieno[3,2-c]pyridin-5-yl]-(4-methoxy-piperidin-1-yl)-methanone,
2-(1-isopropyl-piperidin-4-yloxy)-6,7-dihydro-4H-thieno[3,2-c]pyridine-5-carboxylic acid isopropylamide,
1-[2-(1-isopropyl-piperidin-4-yloxy)-6,7-dihydro-4H-thieno[3,2-c]pyridin-5-yl]-butan-1-one,
1-[2-(1-isopropyl-piperidin-4-yloxy)-6,7-dihydro-4H-thieno[3,2-c]pyridin-5-yl]-pentan-1-one,
1-[2-(1-isopropyl-piperidin-4-yloxy)-6,7-dihydro-4H-thieno[3,2-c]pyridin-5-yl]-2-(4-methyl-cyclohexyl)-ethanone, and
(2-chloro-phenyl)-[2-(1-isopropyl-piperidin-4-yloxy)-6,7-dihydro-4H-thieno[3,2-c]pyridin-5-yl]-methanone.

22. The compound according to claim 1, selected from the group consisting of:
2-(1-isopropyl-piperidin-4-yloxy)-5-methane-sulfonyl-4,5,6,7-tetrahydro-thieno[3,2-c]pyridine,
5-(butane-1-sulfonyl)-2-(1-isopropyl-piperidin-4-yloxy)-4,5,6,7-tetrahydro-thieno[3,2-c]pyridine,
5-benzenesulfonyl-2-(1-isopropyl-piperidin-4-yloxy)-4,5,6,7-tetrahydro-thieno[3,2-c]pyridine,
2-(1-isopropyl-piperidin-4-yloxy)-5-(toluene-2-sulfonyl)-4,5,6,7-tetrahydro-thieno[3,2-c]pyridine,
2-(1-isopropyl-piperidin-4-yloxy)-5-(toluene-3-sulfonyl)-4,5,6,7-tetrahydro-thieno[3,2-c]pyridine,
2-(1-isopropyl-piperidin-4-yloxy)-5-(toluene-4-sulfonyl)-4,5,6,7-tetrahydro-thieno[3,2-c]pyridine,
5-(4-ethyl-benzenesulfonyl)-2-(1-isopropyl-piperidin-4-yloxy)-4,5,6,7-tetrahydro-thieno[3,2-c]pyridine,
2-(1-isopropyl-pyrrolidin-3-yloxy)-6,7-dihydro-4H-thieno[3,2-c]pyridine-5-carboxylic acid isopropylamide,
[2-(1-isopropyl-pyrrolidin-3-yloxy)-6,7-dihydro-4H-thieno[3,2-c]pyridin-5-yl]-morpholin-4-yl-methanone,
2-ethyl-1-[2-(1-isopropyl-pyrrolidin-3-yloxy)-6,7-dihydro-4H-thieno[3,2-c]pyridin-5-yl]-butan-1-one,
1-[2-(1-isopropyl-pyrrolidin-3-yloxy)-6,7-dihydro-4H-thieno[3,2-c]pyridin-5-yl]-2-(4-methyl-cyclohexyl)-ethanone,
(2-chloro-phenyl)-[2-(1-isopropyl-pyrrolidin-3-yloxy)-6,7-dihydro-4H-thieno[3,2-c]pyridin-5-yl]-methanone,
(3-chloro-phenyl)-[2-(1-isopropyl-pyrrolidin-3-yloxy)-6,7-dihydro-4H-thieno[3,2-c]pyridin-5-yl]-methanone,
(2,3-difluoro-phenyl)-[2-(1-isopropyl-pyrrolidin-3-yloxy)-6,7-dihydro-4H-thieno[3,2-c]pyridin-5-yl]-methanone,
[2-(1-isopropyl-pyrrolidin-3-yloxy)-6,7-dihydro-4H-thieno[3,2-c]pyridin-5-yl]-pyrrolidin-1-yl-methanone,
1-[2-(1-isopropyl-pyrrolidin-3-yloxy)-6,7-dihydro-4H-thieno[3,2-c]pyridin-5-yl]-3-methyl-butan-1-one, and
2-(1-isopropyl-pyrrolidin-3-yloxy)-5-methane-sulfonyl-4,5,6,7-tetrahydro-thieno[3,2-c]pyridine.

23. The compound according to claim 1, selected from the group consisting of:
5-benzenesulfonyl-2-(1-isopropyl-pyrrolidin-3-yloxy)-4,5,6,7-tetrahydro-thieno[3,2-c]pyridine,
2-(1-isopropyl-pyrrolidin-3-yloxy)-5-(toluene-3-sulfonyl)-4,5,6,7-tetrahydro-thieno[3,2-c]pyridine,
5-(4-ethyl-benzenesulfonyl)-2-(1-isopropyl-pyrrolidin-3-yloxy)-4,5,6,7-tetrahydro-thieno[3,2-c]pyridine,
2-(1-isopropyl-pyrrolidin-3-yloxy)-5-(propane-2-sulfonyl)-4,5,6,7-tetrahydro-thieno[3,2-c]pyridine,
[2-(3-morpholin-4-yl-propoxy)-6,7-dihydro-4H-thieno[3,2-c]pyridin-5-yl]-phenyl-methanone,
2-(3-morpholin-4-yl-propoxy)-5-(toluene-2-sulfonyl)-4,5,6,7-tetrahydro-thieno[3,2-c]pyridine,
2-(3-morpholin-4-yl-propoxy)-6,7-dihydro-4H-thieno[3,2-c]pyridine-5-carboxylic acid (3-phenyl-propyl)-amide,
[2-(3-morpholin-4-yl-propoxy)-6,7-dihydro-4H-thieno[3,2-c]pyridin-5-yl]-(4-phenyl-piperidin-1-yl)-methanone,
[4-(4-methoxy-phenyl)-piperazin-1-yl]-[2-(3-morpholin-4-yl-propoxy)-6,7-dihydro-4H-thieno[3,2-c]pyridin-5-yl]-methanone,
and pharmaceutically acceptable salts thereof.

24. The compound according to claim 1, selected from the group consisting of
morpholin-4-yl-[2-(3-piperidin-1-yl-propoxy)-6,7-dihydro-4H-thieno[3,2-c]pyridin-5-yl]-methanone,
[2-(3-piperidin-1-yl-propoxy)-6,7-dihydro-4H-thieno[3,2-c]pyridin-5-yl]-pyrrolidin-1-yl-methanone,
morpholin-4-yl-[2-(3-pyrrolidin-1-yl-propoxy)-6,7-dihydro-4H-thieno[3,2-c]pyridin-5-yl]-methanone,
(4-methyl-piperazin-1-yl)-[2-(3-pyrrolidin-1-yl-propoxy)-6,7-dihydro-4H-thieno[3,2-c]pyridin-5-yl]-methanone,
2-(3-pyrrolidin-1-yl-propoxy)-6,7-dihydro-4H-thieno[3,2-c]pyridine-5-carboxylic acid benzylamide,
2-ethyl-1-[2-(3-pyrrolidin-1-yl-propoxy)-6,7-dihydro-4H-thieno[3,2-c]pyridin-5-yl]-butan-1-one,
3-methyl-1-[2-(3-pyrrolidin-1-yl-propoxy)-6,7-dihydro-4H-thieno[3,2-c]pyridin-5-yl]-butan-1-one,
2-(3-pyrrolidin-1-yl-propoxy)-5-(toluene-2-sulfonyl)-4,5,6,7-tetrahydro-thieno[3,2-c]pyridine,
(4-phenyl-piperazin-1-yl)-[2-(3-pyrrolidin-1-yl-propoxy)-6,7-dihydro-4H-thieno[3,2-c]pyridin-5-yl]-methanone,
[2-(1-isopropyl-piperidin-4-yloxy)-6,7-dihydro-4H-thieno[3,2-c]pyridin-5-yl]-morpholin-4-yl-methanone,
[2-(1-isopropyl-piperidin-4-yloxy)-6,7-dihydro-4H-thieno[3,2-c]pyridin-5-yl]-(4-methoxy-piperidin-1-yl)-methanone,
2-(1-isopropyl-piperidin-4-yloxy)-6,7-dihydro-4H-thieno[3,2-c]pyridine-5-carboxylic acid isopropylamide,
1-[2-(1-isopropyl-piperidin-4-yloxy)-6,7-dihydro-4H-thieno[3,2-c]pyridin-5-yl]-pentan-1-one,
(2-chloro-phenyl)-[2-(1-isopropyl-piperidin-4-yloxy)-6,7-dihydro-4H-thieno[3,2-c]pyridin-5-yl]-methanone,
2-(1-isopropyl-piperidin-4-yloxy)-5-(toluene-2-sulfonyl)-4,5,6,7-tetrahydro-thieno[3,2-c]pyridine,
1-[2-(1-isopropyl-pyrrolidin-3-yloxy)-6,7-dihydro-4H-thieno[3,2-c]pyridin-5-yl]-2-(4-methyl-cyclohexyl)-ethanone,
and pharmaceutically acceptable salts thereof.

25. A pharmaceutical composition, comprising a therapeutically effective amount of a compound according to claim 1 as well as a pharmaceutically acceptable carrier and/or adjuvant.

* * * * *